(12) United States Patent
Tan et al.

(10) Patent No.: US 12,017,972 B2
(45) Date of Patent: Jun. 25, 2024

(54) ALL-AROMATIC LIQUID-CRYSTALLINE HOMO-POLYIMIDES WITH AROMATIC ENDGROUPS AND CROSSLINKED PRODUCTS THEREFROM

(71) Applicant: Government of the United States, as represented by the Secretary of the Air Force, Wright-Patterson AFB, OH (US)

(72) Inventors: Loon-Seng Tan, Centerville, OH (US); Zhenning Yu, Beavercreek, OH (US)

(73) Assignee: The Government of the United States of America as Represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 18/299,375

(22) Filed: Apr. 12, 2023

(65) Prior Publication Data

US 2024/0109837 A1    Apr. 4, 2024

Related U.S. Application Data

(60) Provisional application No. 63/405,999, filed on Sep. 13, 2022.

(51) Int. Cl.
*C07C 217/90* (2006.01)
*C07C 213/06* (2006.01)
*C08G 73/10* (2006.01)

(52) U.S. Cl.
CPC .......... *C07C 217/90* (2013.01); *C07C 213/06* (2013.01); *C08G 73/1071* (2013.01)

(58) Field of Classification Search
None
See application file for complete search history.

(56) References Cited

U.S. PATENT DOCUMENTS

| | | | |
|---|---|---|---|
| 5,196,506 | A | 3/1993 | Tamai et al. |
| 5,606,014 | A | 2/1997 | Connell et al. |
| 6,124,035 | A | 9/2000 | Connell et al. |
| 6,350,817 | B1 | 2/2002 | Connell et al. |
| 10,988,437 | B1 | 4/2021 | Tan et al. |
| 11,608,310 | B1 | 3/2023 | Tan et al. |

FOREIGN PATENT DOCUMENTS

| | | | |
|---|---|---|---|
| JP | 64000121 | * | 1/1989 |
| JP | 2000248252 A | | 9/2000 |
| JP | 3302109 | * | 7/2002 |
| JP | 4467662 B2 | | 5/2010 |

OTHER PUBLICATIONS

Matsuo et al. JP 3302109 Machine English Translation (Year: 2002).*
Machine English translation of Ikeda et al. (JP 64000121) published Jan. 5, 1989 (Year: 1989).*
Nye, S. A.: Polyimides synthesized from 4,4'-(1,2-ethynediyl)bis(phthalic anhydride). Journal of Polymer Science, Part A: Polymer Chemistry 1990, 28, 2633-40.
Pardey, R.; Zhang,A.; Gabori, P. A.; Harris, F. W.; Stephen Z. D. Cheng, S. Z. D.; Jerry Adduci, J.; Facinelli, J. V.; Lenz, R. W.; Monotropic Liquid Crystal Behavior in Two Poly(ester imides)with Even and Odd Flexible Spacers Macromolecules 1992, 25, 5060-5068.
Inoue, T.; Kakimoto, M.-A.; Imai, Y.; Watanabe, J.: First Observation of a Thermotropic Liquid Crystal in a Simple Polyimide Derived from 1,11-Diaminoundecane and 4,4"-Terphenyltetracarboxylic Acid. Macromolecules 1995, 28, 6368-6370.
Inoue, T.; Kumagai, K.; Kakimoto, M.; Imai, Y.; Watanabe, J.; High-Pressure Synthesis and Properties of Aliphatic-Aromatic Polyimides via Nylon-Salt-Type Monomers Derived from Aliphatic Diamines with Pyromellitic Acid and Biphenyltetracarboxylic Acid Macromolecules 1997, 30, 1921-1928.
Kaneko, T. I. Imamura, K.: Watanabe, J.; Reversible Crystal Deformation Observed in the Main-Chain Type of Liquid Crystalline Polyimide, Macromolecules 1997, 30, 4244-4246.
Sato, M.; Ujiie, S.; Tada, Y.; Kato, T. Semirigid: Homo- and Copoly(Imide-Carbonate)s Based on 3,4,3 ,4-p-Terphenyltetracarboxdiimide. High Performance Polymers 1998, 10, 155-162.
Fernberg, P; Guan Gong, G.; Mannberg, P.; Tsampas, S.; Development of novel high Tg polyimide-based composites. Part I: RTM processing properties Journal of Composite Materials 2018, vol. 52(2) 253-260.
Abbott, A.; Gibson, T.; Tandon, G. P.; Hu, L.; Avakian, R.; Baur, J.; Koerner, H.: Melt extrusion and additive manufacturing of a thermosetting polyimide. Additive Manufacturing 2021, 37, 101636.
Zhang, H.; Wang, W.; Chen, G.; Zhang, A.; Fang, X.: Melt-Processable Semicrystalline Polyimides Based on 1,4-Bis(3,4-dicarboxyphenoxy)benzene Dianhydride (HQDPA): Synthesis, Crystallization, and Melting Behavior. Polymers 2017, 9.
Noël, C.; Navard, P.: Liquid crystal polymers. Progress in Polymer Science 1991, 16, 55-110.
Connell, J. W.; Smith, J. G., Jr.; Hergenrother, P. M.: Oligomers and polymers containing phenylethynyl groups. Journal of Macromolecular Science, Reviews in Macromolecular Chemistry and Physics 2000, C40, 207-230.

(Continued)

*Primary Examiner* — Sudhakar Katakam
*Assistant Examiner* — Jennifer C Sawyer
(74) *Attorney, Agent, or Firm* — AFMCLO/JAZ; James F. McBride

(57) ABSTRACT

A family of low-molecular-weight, main-chain thermotropic liquid-crystalline polyimides (TLC-PI) that are crosslinkable is disclosed. These all-aromatic TLC-PI are derived from (i) wholly aromatic and flexible diamine monomers, in which the linkage between the two aniline-ends contains a relatively high heat-tolerant but flexible chain constituted by two or more units of 1,4-phenoxy or 1,3-phenoxy or in combinations of both. Processes of making and using such all-aromatic TLC-PI is also provided.

1 Claim, 14 Drawing Sheets

(9 of 14 Drawing Sheet(s) Filed in Color)

(56) References Cited

OTHER PUBLICATIONS

Smith, J. G., Jr.; Connell, J. W.: Chemistry and properties of imide oligomers from phenylethynyl-containing diamines. High Performance Polymers 2000, 12, 213-223.
Connell, J. W.; Smith, J. G., Jr.; Hergenrother, P. M.: Properties of imide oligomers containing pendent phenylethynyl groups. High Performance Polymers 1997, 9, 309-321.
Kricheldorf, H. R.: Liquid-crystalline polyimides. Advances in Polymer Science 1999, 141, 83-187.
Takeichi, T.; Tanikawa, M.; Internal Acetylene Unit Linked para to the Aromatic Ring as a Crosslink Site for Polyimide Journal of Polymer Science: Part A: Polymer Chemistry, 1996, vol. 34, 2205-2211.
Meng, Y. Z.; Tjong, S. C.; Hay, A. S.; Morphology, rheological and thermal properties of the melt blends of poly(phthalazinone ether ketone sulfone) with liquid crystalline co polyester Polymer 1998, vol. 39, No. 10, pp. 1845-1850.
Guan, Q.; Picken, S. J.; Sheiko, S. S.; Theo J. Dingemans, T. J.; High-Temperature Shape Memory Behavior of Novel All Aromatic (AB)n-Multiblock Copoly(ester imide)s Macromolecules 2017, 50, 3903-3910.
Liu, S. L.; Chung, T. S.; Geng, J. X.; Zhou, E. L.; Tamai, S.; Phase Transition and Transition Kinetics of a Thermotropic Poly(amide-imide) Derived from 70% Pyromellitic Dianhydride, 30% Terephthaloyl Chloride, and I ,3-Bis [4-(4'-aminophenoxy)cumyl]benzene Macromolecules 2001, 34, 8710-8719.
Guan, Q.; Norder, B.; Chu, L.; Besseling, N. A. M.; Picken, S. J.; Theo J. Dingemans, T. J.; All-Aromatic (AB)n-Multiblock Copolymers via Simple One-Step Melt Condensation Chemistry Macromolecules 2016, 49, 8549-8562.
Tamboli, A. B.; Ghodke, S. D.; Diwate, A. V.; Joshi, M. D.; Ubale, V. P.; Maldar, N. N.: Processable poly(ether ether ketone imide)s. High Performance Polymers 2021, DOI: 10.1177/09540083211055044.
U.S. Appl. No. 16/752,794, filed Jan. 27, 2020.
U.S. Appl. No. 16/752,804, filed Jan. 27, 2020.
U.S. Appl. No. 18/103,860, filed Jan. 31, 2023.
Asanuma, T.; Oikawa, H.; Ookawa, Y.; Yamasita, W.; Matsuo, M.; Yamaguchi, A.: Synthesis of thermotropic liquid crystal polyimide and its properties. Journal of Polymer Science, Part A: Polymer Chemistry 1994, 32, 2111-18.
Zheng, B.; Ree, B.; Yu, Z.; Tan, L.; Koerner, H.; Development of high-performance nematic liquid crystalline polyimides (LCPI) for 3D printing, Presentation Aug. 2022.
U.S. Appl. No. 18/299,092, filed Apr. 12, 2023.
U.S. Appl. No. 18/299,096, filed Apr. 12, 2023.
U.S. Appl. No. 18/299,100, filed Apr. 12, 2023.
U.S. Appl. No. 18/299,090, filed Apr. 12, 2023.
U.S. Appl. No. 18/299,353, filed Apr. 12, 2023.
CAS Registry No. 121162-22-9.

\* cited by examiner

ALL-AROMATIC LIQUID-CRYSTALLINE HOMO-POLYIMIDES WITH AROMATIC ENDGROUPS AND CROSSLINKED PRODUCTS THEREFROM

CROSS-REFERENCE TO RELATED APPLICATION

The present application claims priority to U.S. Provisional Application Ser. No. 63/405,999 filed Sep. 13, 2022, the contents of which is hereby incorporated by reference in their entry. The present application is related to, but does not claim priority to, U.S. application Ser. No. 14/999,921 which was filed under a secrecy order on Jan. 25, 2017.

RIGHTS OF THE GOVERNMENT

The invention described herein may be manufactured and used by or for the Government of the United States for all governmental purposes without the payment of any royalty.

FIELD OF THE INVENTION

The present invention relates to a family of thermally crosslinkable, low-molecular-weight, main-chain thermotropic liquid-crystalline polyimides and processes of making and using same.

BACKGROUND OF THE INVENTION

Applicants disclose compositions and methods of manufacture for a family of low-molecular-weight, main-chain thermotropic liquid-crystalline polyimides (TLC-PI) that are crosslinkable. These all-aromatic TLC-PI are derived from (i) wholly aromatic and flexible diamine monomers, in which the linkage between the two aniline-ends contains a relatively high heat-tolerant but flexible chain constituted by two or more units of 1,4-phenoxy or 1,3-phenoxy or in combinations of both. These bis(aniline) or di-aniline monomers are designated as MPDA, and the diketo-containing MPDA derivatives are designated as MPKDA, and (ii) a mesogenic dianhydride that can be either thermally non-nonreactive such as pyromellitic dianhydride (PMDA) and terphenyl dianhydride (TPDA) or a diphthalic dianhydride (DPA) that contains one or more thermally reactive and crosslinkable moieties similar to that of phenylethynyl (PE). Preferably in both the MPDA and MPKDA diamines, 1,4-substituted phenoxy or paraphenylene-oxy moieties are situated at both aniline-ends of the monomer to provide the necessary aspect ratio for thermotropic LC properties when combined with a mesogenic dianhydride. In addition, the thermally crosslinkable TLCP-PI is endcapped by either a non-reactive anhydride such as phthalic anhydride (PA) or thermally reactive one such as 4-phenylethynylanhydride (PEPA). The LC-to-isotropic phase transition temperatures of our TLCP-PI, particularly those based on TPDA ($T_{Lc\text{-}iso}$~250-320° C.; Table 5 & FIG. 8) and PEDPA ($T_{Lc\text{-}iso}$~250-260° C.; FIG. 11) are well below the that of high-molecular-weight PMDA-BACB ($T_{Lc\text{-}iso}$~310° C.) and the curing temperatures of thermosetting polyimides [T(cure)$_{onset}$>300° C.]. This feature has the flexibility advantage in modifying the ink materials to meet varying processing conditions in additive manufacturing of devices and components that require high-temperature polymers.

SUMMARY OF THE INVENTION

A family of low-molecular-weight, main-chain thermotropic liquid-crystalline polyimides (TLC-PI) that are crosslinkable is disclosed. These all-aromatic TLC-PI are derived from (i) wholly aromatic and flexible diamine monomers, in which the linkage between the two aniline-ends contains a relatively high heat-tolerant but flexible chain constituted by two or more units of 1,4-phenoxy or 1,3-phenoxy or in combinations of both. Processes of making and using such all-aromatic TLC-PI is also provided.

Additional objects, advantages, and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 9 depicts (a) repeated DSC scans of sample 07-47-1: first heating scan (black) to 450° C. and 2nd heating scan (red) to 400° C.; (b) depicts POM images of 07-47-1 taken at different temperatures, indicating its isotropic melt at 280° C. and being liquid crystalline ~250-260° C. before curing at temperature above 320° C.

DETAILED DESCRIPTION OF THE INVENTION

Definitions

Figure 1:
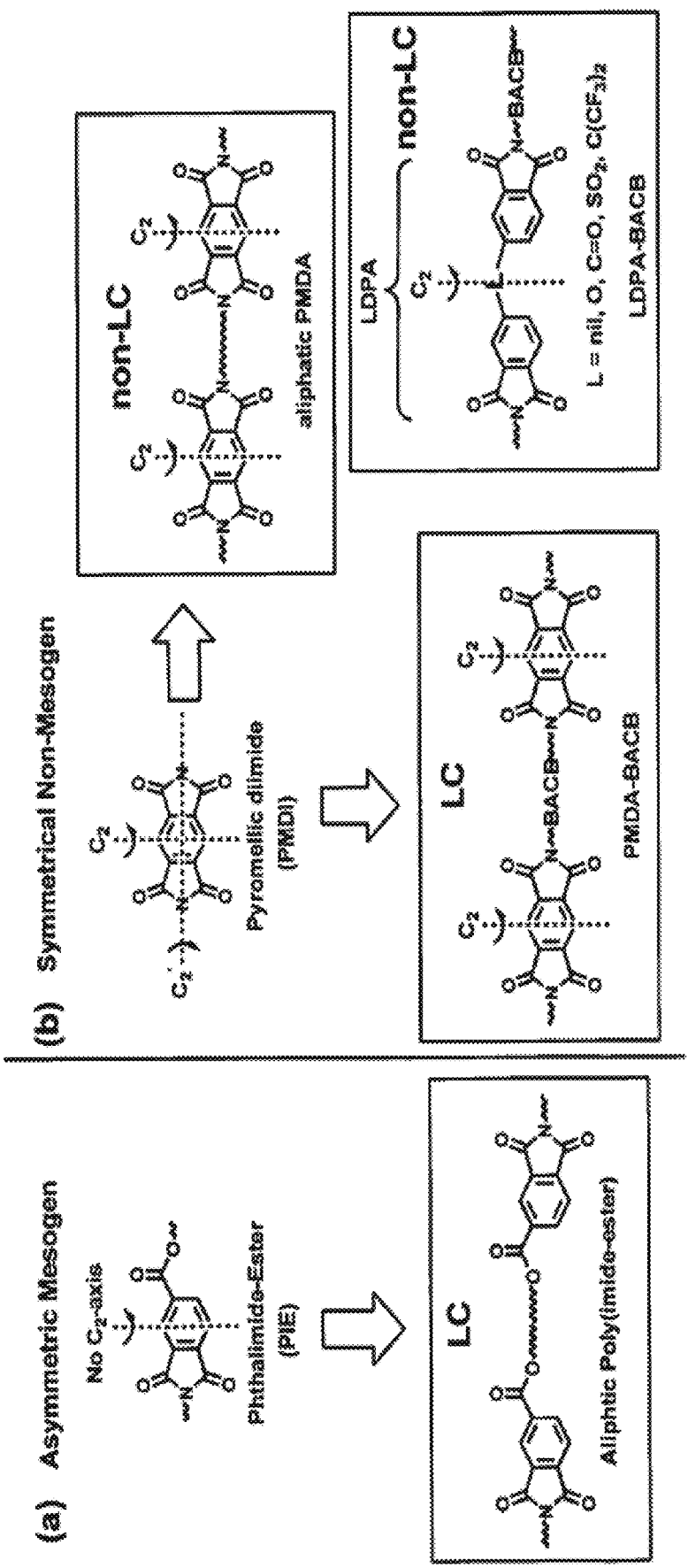
FIG. 1 depicts the structural comparisons of (a) an asymmetric phthalimide-ester (PIE) mesogen and (b) the symmetrical pyromellitimide, PMDI and linked diphthalic dianhydride (LDPA). and (in boxes) the corresponding repeat units in their polyimides that are liquid crystalline (LC) or non-LC. The linking group (L) is generally a short linker and the wavy symbol represent flexible chains such as $(CH_2)_n$, $—(CH_2CH_2O)_n—$. BACB is a highly aromatic and flexible linker derived from the diamine, 1,3-bis[4'-(4"-aminophenoxy)cumyl)]benzene.

Unless specifically stated otherwise, as used herein, the terms "a", "an" and "the" mean "at least one".

As used herein, the terms "include", "includes" and "including" are meant to be non-limiting.

As used herein, the words "about," "approximately," or the like, when accompanying a numerical value, are to be construed as indicating a deviation as would be appreciated by one of ordinary skill in the art to operate satisfactorily for an intended purpose.

As used herein, the words "and/or" means, when referring to embodiments (for example an embodiment having elements A and/or B) that the embodiment may have element A alone, element B alone, or elements A and B taken together.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

DPA is the abbreviation for Di-(Phthalic Dianhydride) or diphthalic dianhydride.

DSC is the abbreviation for Differential scanning calorimetry.

EDPA is the abbreviation for compound with a chemical name of "ethynyl-4,4'-di(phthalic anhydride)."

EFPE-DPA is the abbreviation for compound with a chemical name of "4,4'-(2-fluoro-1,4-phenylene)bis(ethyne-2,1-diyl)diphthalic anhydride."

1,4EPE-DPA is the abbreviation for compound with a chemical name of "4,4'-(1,4-phenylenebis(ethyne-2,1-diyl)) diphthalic anhydride."

1,3EPE-DPA is the abbreviation for compound with a chemical name of "4,4'-(1,3-phenylenebis(ethyne-2,1-diyl)) diphthalic anhydride."

EPPE-DPA is the abbreviation for compound with chemical names of "4'-((3,4-dicarboxyphenyl)ethynyl)biphenyl-3,4-dicarboxylic dianhydride," and "4,4'-(biphenyl-4,4'-diyl-bis(ethyne-2,1-diyl))diphthalic anhydride."

LC is the abbreviation for liquid-crystalline or liquid-crystallinity.

LDPA is the abbreviation for linked di(phthalic dianhydride) moiety.

MPDA is the abbreviation for multi-phenoxy-linked 4,4'-dianiline.

MPKDA is the abbreviation for the diketo-containing MPDA derivatives.

PE-DPA or PEDPA is the abbreviation for compound with a chemical name of "4'((3,4-dicarboxyphenyl)ethynyl)biphenyl-3,4-dicarboxylic dianhydride."

PIE is the abbreviation for "phthalimide-ester" moiety.

PMDA is the abbreviation for pyromellitic dianhydride.

PMDI is the abbreviation for pyromellitimide moiety.

POM is the abbreviation for Polarization Optical Microscopy.

NR-DPA is the abbreviation for Non-Reactive Di-(Phthalic Dianhydride).

R-DPA is the abbreviation for Reactive Di-(Phthalic Dianhydride).

TPDA is the abbreviation for compound with a chemical name of "terphenyl-3,3",4,4"-dianhydride".

TLC is the abbreviation for thermal crystalline or thermal crystallinity.

PA is the abbreviation for phthalic anhydride.

PEPA is the abbreviation for 4-phenylethynylphthalic anhydride.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Additive manufacturing or 3-dimensional (3D) printing makes three-dimensional objects by building up material, based upon design data provided from a computer aided design (CAD) system. One technique is to deposit a resolidifiable material in a predetermined pattern, according to design data provided from a CAD system, with the build-up of multiple layers forming the object. The resolidifiable "ink" materials can be either in the form of filaments or powdered resins.

Fused Filament Fabrication (or FFF) is one type of additive manufacturing (AM) technique. Materials used for fused filament fabrication are typically thermoplastic (linear) polymers in the form of filaments. The filaments are melted in a "printer" head and extruded onto a deposition surface, and form a solid layer upon cooling. Multiple layers are deposited one atop the other. The complete ensemble of the layers forms the 3-dimensional article.

Selective Laser Sintering (SLS) is another type of AM technique that uses a laser as the power source to sinter powdered material, aiming the laser focus automatically at points in space defined by a 3D model, binding the material together to create a solid structure. For hot environment applications such as those that can be found in aerospace applications, state of the art 3D printed thermoplastic articles lack key properties that enable use as engine externals or brackets and fixtures in cooler sections of an engine, ducting for cabin air, etc. Currently, the commonly used thermoplastic materials used in FFF or SLS technology are limited in use temperature and have poor thermo-oxidative stability. For example, state-of the-art 3D filament printable aerospace grade thermoplastics such as ULTEM™ 1010, and ULTEM™ 9085 have use temperatures of 190° C. and 160° C., respectively, and are susceptible to creep during the 3D printing process. These thermoplastic melts are isotropic, that is they are not liquid-crystalline.

Accordingly, there is a need for new materials and methods for use in FFF, SLS, and other additive manufacturing techniques that demonstrate improved thermal stability, possess higher service-temperatures and have processability like thermotropic liquid-crystalline polymers (TLCP). In TLCP systems, because of the generally lower melt viscosity associated with columnal or anisotropic flow as the result of the polymer-chain alignment in the liquid crystalline phase, which would likely to occur in the nozzle of a 3D printer, it is expected that liquid-crystalline character of the ink materials and ability to tailor such character would be advantageous to the above-mentioned additive manufacturing methods.

Liquid-Crystallinity. An important requirement in the processing of thermotropic liquid-crystalline polymer (TLCP) is having a workable LC temperature window (≥20° C.) for the TLCP to sustain the LC phase or anisotropy via dynamic molecular ordering and occurring well below a prescribed temperature for the onset of a well-defined cross-linking reaction in continuing heating to the temperature range well before the onset of anticipated degradation of polymer chains; or upon cooling at the end of LC mesophase that can result in a semicrystalline morphology. Both covalently crosslinked (amorphous) and (non-covalently crosslinked) semicrystalline products are known to possess improved mechanical, thermal and solvent resistant properties than the analogous TLCPs that are non-crosslinked and amorphous.

In thermotropic LC polymers, the transition temperatures from a crystal phase to a liquid crystal phase (LC), which may consist of one or more distinctly different LC textures observed under a polarized optical microscope (OPM), and finally to an isotropic phase, are strongly dependent on the molecular structures of mesogenic component and polymer chain as well as the molecular weight, as evidenced by the work of S. Hocine and M. H. Soft Matter, 2013, vol. 9, pp, 5839-5861. The LC temperature range is generally determined from the onset temperature at which the crystalline phase (ordered and rigid) of LCP begins to transform to liquid-crystalline phase (ordered but mobile) to the temperature at which significant amount of isotropic melt (biphasic) is observed. This former temperature is denoted as "crystal-to-liquid-crystal" or $T_{Crys-LC}$, and the latter is designated as $T_{iso}$.

For thermotropic LCP, there are generally two types of LC morphology depending on the structures driven by the dynamics of the molecular-to-meso-scale arrangements of the mesogenic units in the polymer chains. When the morphology of the LC phase shows only an orientational ordering of the mesogenic units in the LCP following a general direction or a director, and no positional ordering, this relatively simple LC phase is designated as "nematic" phase. On the other hand, the morphology of LC phase designated as "smectic" mesophase is more complex. It has a lamellar or layered structure that is characterized by the state of being both orientationally and positionally ordered, in which the mesogens self-organize in parallel layers. In addition, the general orientation of the parallel mesogens in one layer with respect to similarly parallel mesogens in the next layers can be "in-line" (Smectic-A), "offset" (Smectic B) or "offset and tilted" (Smectic C). Therefore, for the smectic morphology, one or more thermal and associated phase transition temperatures may be observed between $T_{Crys-CL}$ and $T_{iso}$.

The viscosity of the LC phase is a critical determinant in enhancing the processing ease for thermotropic LCP into fibers or oriented films. The macromolecules of LCPs are very stiff and generally have a rigid-rod structure. These rod-like macromolecules tend to align more easily than the coil-like macromolecules of amorphous thermoplastics along the flow or sheer direction under appropriate processing conditions. In comparison with typically linear thermoplastic polymers, the melt viscosity of LCP is generally lowered when they are molecularly aligned; and in many cases, a small amount of LCP added to thermoplastic polymers can result in a significantly lower melt viscosity in comparison to the pure melt of the thermoplastics, as illustrated by the work of Y. Z. Meng, et al. Polymer 1998, vol. 39, pp. 1845-1850.

A special class of thermotropic liquid-crystalline polymer (TLCP) is the main-chain polyimides (PI) which are typically synthesized from the polycondensation of an aromatic dianhydride and a diamine. These traditional thermotropic liquid-crystalline polyimides (TLCP-PI) are constituted by (i) the rigid dianhydride being the mesogen capable of self-aggregation to form the so-called liquid-crystalline (LC) phase, i.e., a mesophase which is a phase between crystal and isotropic melt phases; (ii) the diamine being the flexible and thermally mobile to facilitate the self-aggregation of the mesogenic units. From the structural standpoint of mesogenic anhydrides, there are generally two approach to the synthesis of thermotropic liquid-crystalline polyimides (TLC-PI), namely the utilization of mesogens that are either symmetrical dianhydrides such as pyromellitic dianhydride (PMDA), 3,4,3',4'-biphenyltetracarboxylic dianhydride (BPDA) and TPDA whose symmetry is defined by having a $C_2$-rotation molecular axis and unsymmetrical di(anhydride-ester) with the generic structure, AE-L-AE, in which the AE is an unsymmetrical anhydride, and L is a bivalent linking group (see FIG. 1 for the corresponding imide structures). Other symmetrical dianhydrides are 3,4, 3',4'-benzophenone tetracarboxylic dianhydride (BTDA), 3,4,3',4'-diphenylsulfone tetracarboxylic dianhydride (BSDA) and 4,4'-oxy-di(phthalic anhydride) (ODPA). There have been a number of systematic studies conducted on the syntheses and TLC correlation of various aromatic-aliphatic semirigid polyimides composed of these symmetrical dianhydrides and aliphatic chains in the main chains. A general finding is that most of them are crystalline; and because of their poor mesogenic properties, they are unable to show TLC properties without the inclusion of a traditional biphenyl mesogen in the polymer backbones; thus poly(esterimides) and poly(carbonate-imides) that were composed of asymmetric N-phenylphthalimide rings form LC phases. For examples, the work of M. Sato, et al. High Performance Polymers 1998, 10, 155-162, and that of T. Inoue, et al. Macromolecules 1995, vol. 28, pp. 6368-6370, have shown that the-thermotropic liquid crystals for the simple polyimides which consist of symmetrical imide rings and polymethylene spacers appear to be only that derived from TPDA and 1,11-diaminoundecane.

Pyromellitic dianhydride (PMDA) is a common, structurally rigid dianhydride, and the key building block for the well-known aromatic polyimide, namely Kapton, which is a semi-crystalline polymer. As illustrated by the work of H. R. Kricheldorf, et al. Makromolekulare Chemie, 1993, vol. 194, pp 1209-24, and that of M. Sato, et al. Polymer Journal 2002, vol. 34, pp. 158-165, while PMDA meets the structural rigidity of being an LC mesogen, a large number of polyimides and poly(ester-mide)s derived from PMDA and aliphatic components only form isotropic (non-LC) melts. Therefore, it was rather unusual that a thermotropic liquid-crystalline polyimide (TLC-PI) was reported in 1994 by Asanuma et al. Journal of Polymer Science, Part A: Polymer Chemistry 1994, 32, 2111-18. This particular polyimide, designated as PMDA-BACB, was synthesized from PMDA and a highly aromatic but flexible diamine, namely, 1,3-bis [4'-(4"-aminophenoxy)cumyl]benzene (BACB).

However, while PMDA-BACB polyimide is a thermotropic liquid crystalline polymer, its LC phase can be achieved at temperatures well above 300° C. and the associated melt viscosity is deemed impractical for the 3D-printing of thermoplastic or thermosetting polyimides. These processing issues are stemming from the exceeding strong propensity of the PMDA moieties to aggregate. Therefore, there is a need for non-PMDA dianhydrides that can lead to LC phase at or below 300° C. and/or are capable of thermal crosslinking at temperatures after LC transition temperatures.

Non-PMDA mesogenic dianhdrides with higher aspect ratios: A special family of rigid dianhydrides is based on α,ω-diphthalic dianhydride (DPA) motif, designated here as L(DPA), with the generic structure,

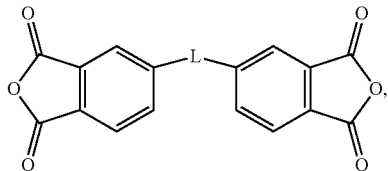

and formula as PA-L-PA, where PA is phthalic anhydride and L is direct bond or an aromatic and/or conjugated connector. The simplest L(DPA) dianhydride, namely, BPDA (3,3',4,4'-biphenyltetracarboxylic dianhydride; L=direct bond) is not mesogenic even when combined with the very flexible aliphatic, α,ω-(CH$_2$)$_n$, chains to enable the resulting polyimides to be thermotropic liquid-crystalline (TLC). Further, when the two PA units are connected by the most rigid two-carbon unit, namely the ethynyl bridge, the resulting ethynyl-diphthalic dianhdride) or EDPA in combination with the LC-promoting, highly aromatic diamine BACB, the resulting polyimide, EDPA-BACB is also not mesogenic.

However, when the two PA units are connected by a longer paraphenylene bridge, the resulting "higher-aspect-ratio" dianhydride, namely, TPDA (3,3',4,4'-p-terphenyltetracarboxdianhydride; L=paraphenylene) and diamines containing similar aliphatic chains did indeed result in TLC-polyimides, as shown by the work of M. Sato, et al. Macromolecular Chemistry and Physics 1996, vol. 197, pp. 2765-2774. Thus, a TLC-PI can be obtained with the TPDA-BACB combination.

Figure 2:
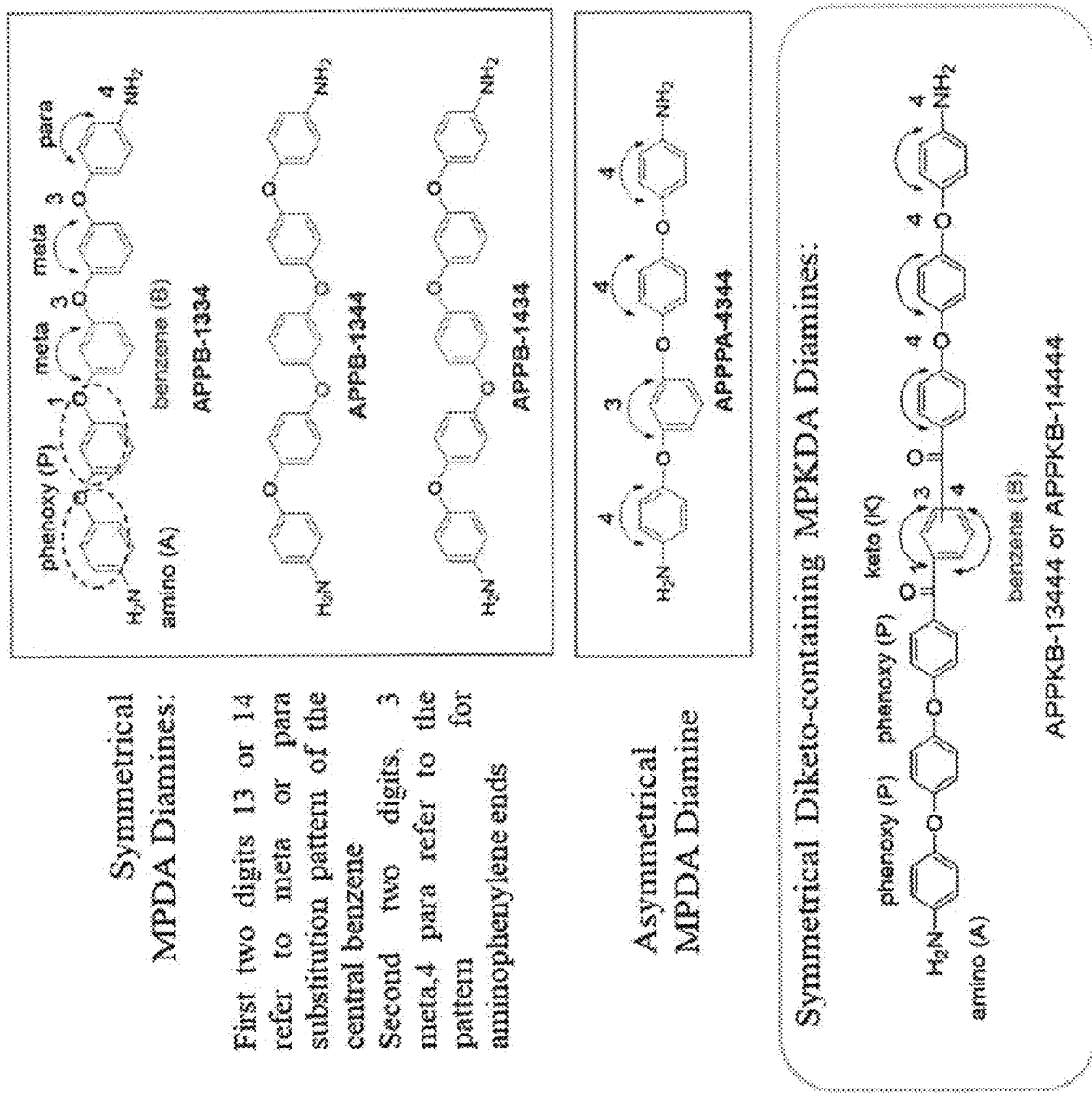
FIG. 2 depicts the structures and coding of "multiple phenoxy di-aniline" (MPDA) and "multiple phenoxy di-keto di-aniline" (MP diamines.

However, because of the aliphatic cumyl (Me2C<) groups in the structure of BACB, the upper limit for high-temperature tolerance would be limited and replacing them with moieties that does not contain any sp3-carbon, similar or smaller in size, and amenable to thermally induced flexibility. Such moiety can be found in the appropriately linked phenoxy and oxyphenylene (—O—C6H4-) structures for all-aromatic diamines that can enable liquid-crystallinity in polyimides when combined with mesogenic dianhydrides. Described here are some of these multiple phenoxy-linked di-aniline (MPDA) monomers and a special MPDA monomer, namely, APPKB-13444 that has a central meta (1,3)-dibenzoylbenzene moiety, in which structure the asymmetric placements of two carbonyl (keto) groups between two separate sets of phenylene rings have apparently suppressed the proclivity of benzophenone moiety in polyimide toward forming crystalline phase and have enhanced promoting the LC-phase instead. The structures and coding of these MPDA diamines are depicted in FIG. 2.

Design and Synthesis of MPDA diamines. As the flexible diamine with the para-oriented 4-aminophenoxy endgroups will provide higher aspect ratio than the meta-oriented 3-aminophenoxy endgroups in the resulting N-phenylphthalimide units to enhance the likelihood of liquid-crystallinity in conjunction with rigidly linked diphthalic dianhydrides (LDPA) to form polyimides, the MPDA diamines all share this common structural and reactivity feature. However, the flexible bis(3-aminophenoxy)1,3-benzene (BAPB), which is a commercially available diamine was used for comparison purposes to validate the requirement of structural motif of (4-aminophenoxy)-L-(4-aminophenyl) to promote liquid crystallinity in the polyimides, MPDA-LPDA.

Figure 3:
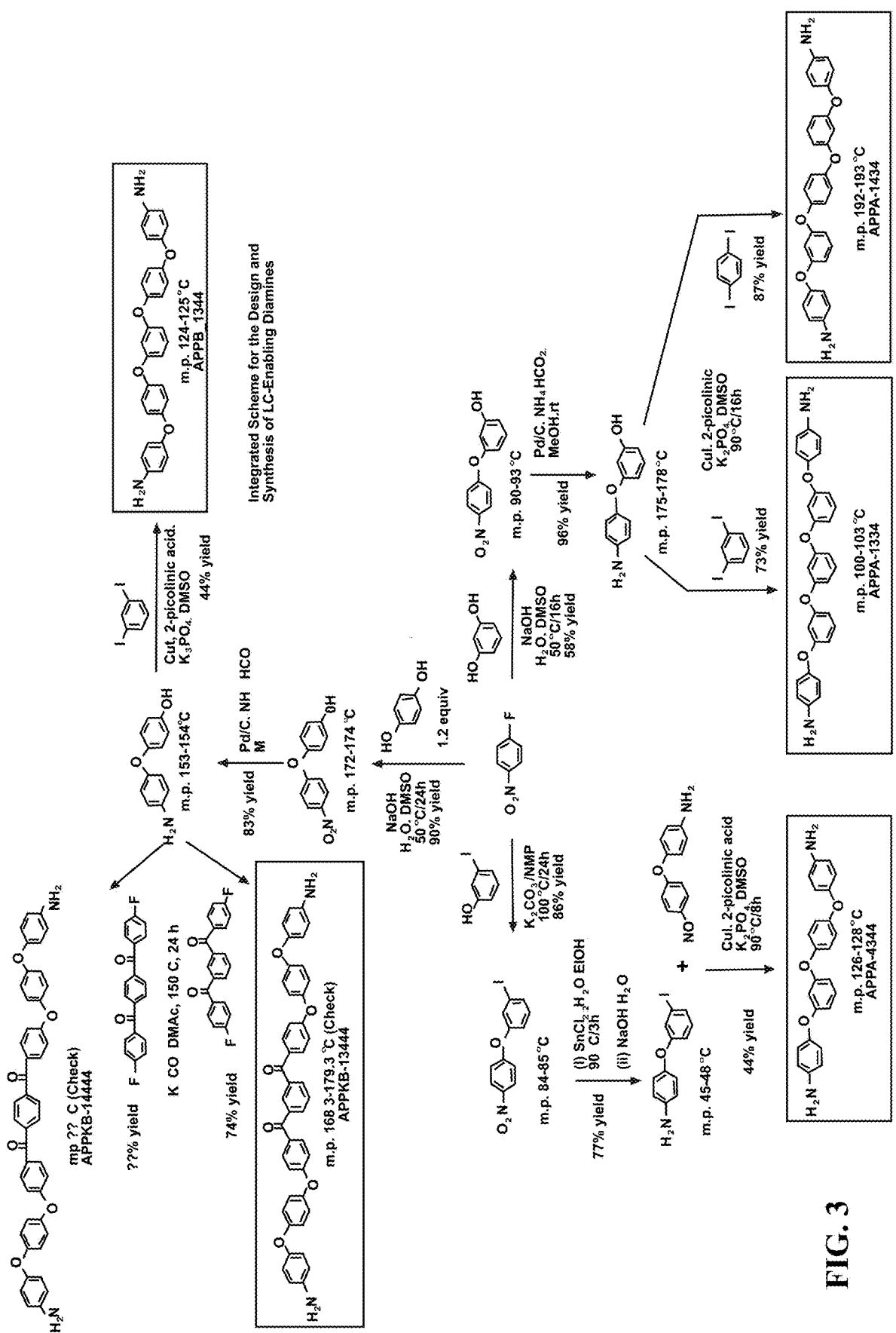
FIG. 3 depicts the integrated synthetic scheme for the LC-enabling MPDA diamines

With reference to FIG. 3, our integrated synthesis of MPDA diamines starts with 4-nitrofluobenzene which would lead to 4-hydroxyphenyl-, 4-nitrophenoxy and 4-aminophenoxy-containing arylether. Aromatic nucleophilic substitution reaction was used exclusively in grand scheme. When the displaced halide was not activated and/or in the meta position, iodide as the leaving group and copper catalyst were required for moderate-good yields of the substituted products. For the synthesis of the 1,3-dibenzoylbenzene-containing diamine, APPKB-13444, the requisite aromatic difluoride precursor, 3-di(fluorobenzoyl)benzene is obtained commercially.

Composition and Synthesis of New Crosslinkable Thermotropic Polyimides: Here, we show that certain non-PMDA dianhydrides in combination with certain MPDA can also form thermotropic LC polyimide. In an embodiment, certain rigidly linked bis(phthaalic dianhydrides) or LDPA's with higher aspect ratios than BPDA and BTDA (Table 2) when in combination with MPDA can result in a new family of thermotropic and crosslinkable LC-PI's. In yet another embodiment, when endcapped with thermally crosslinkable functional group such as phenyethynyls, the resulting MPDA-based reactive oligoimides are thermotropic liquid-crystalline that can be cured in isotropic polyimide thermosets.

Molecular Weight Dependency of Thermotropic Liquid Crystallinity (TLC). Unlike small-molecule liquid-crystals which have polydispersity (PD) or molecular weight distribution (MWD) of unity, linear and thermotropic liquid crystalline polymers (TLCP) are characterized by having MWD values dictated by the polymerization conditions. Therefore, the thermal-transition and morphological characteristics of the corresponding liquid-crystalline phase are also dependent on the MWD of TLCP. Similar to the thermal-transition temperatures for amorphous and semi-crystalline polymers, there is generally a linear correlation between molecular weight and the transition temperatures of thermotropic LCP, including those of the mesophase transitions. Therefore, for consistency in studying the effect of changing the dianhydride from PMDA to those of bis (phthalic diahydride) or DPA with various linking group (L) in MPDA-containing and low-molecular weight polyimides (hereafter generically referred to as "imide oligomers" or "oligoimides"), degree of polymerization (DP) or theoretical number of repeating units (n) is set at 12 by controlled synthesis based on Carothers' equation.

Figure 4:
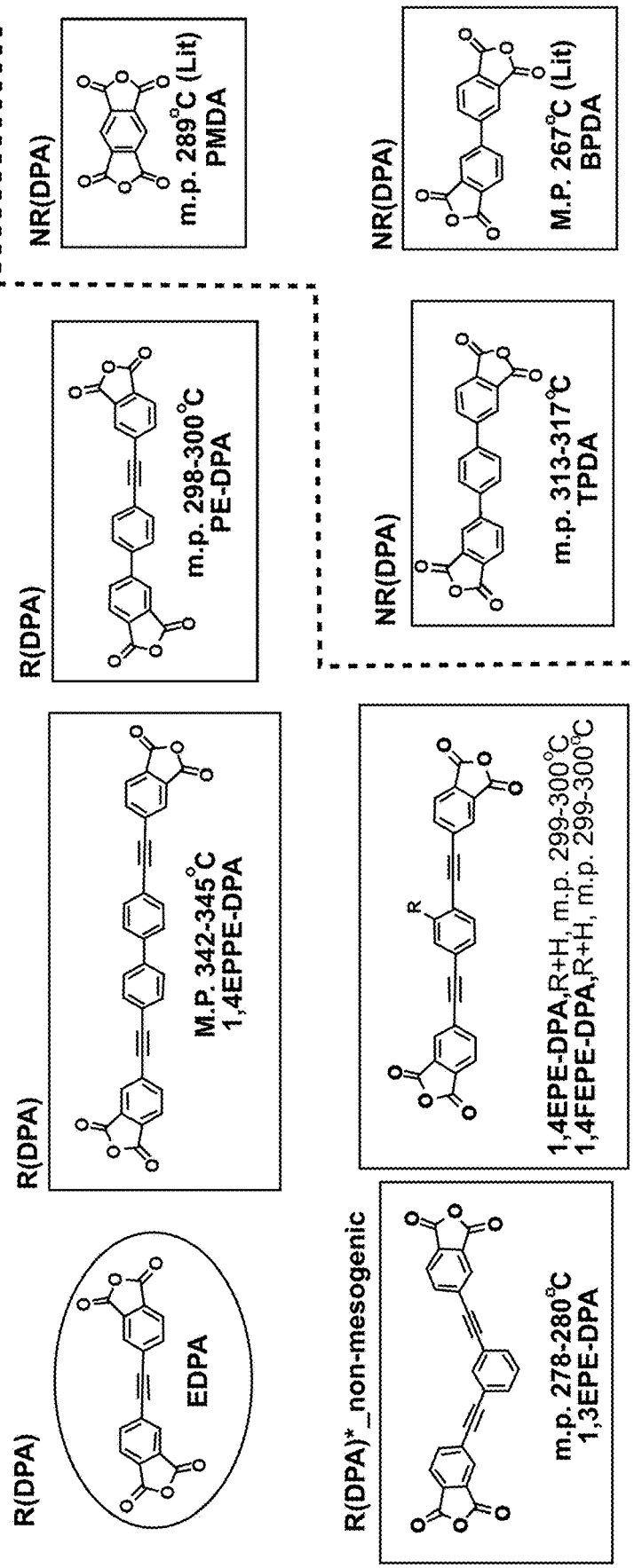
FIG. 4 depicts some examples of Reactive and Non-reactive Mesogenic Dianhydrides (R-DPA & NR-DPA).

Reactive and Non-reactive Mesogenic Dianhydrides (R-DPA & NR-DPA): Our non-PMDA mesogens, i.e., L(DPA),

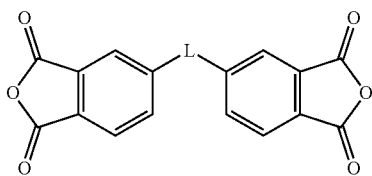

belong to a family of aromatic rod-like dianhydrides with the general composition and formula of (PA)-L-(PA), where PA is phthalic anhydride and L is rigid connector such as an ethynyl (E), a paraphenylene (P), or a rigid moiety of a P-E combination; L can be divided into a reactive (R) group that contains one or more thermally reactive ethynyl (E) units, and non-reactive (NR) group when does not contain any ethynyl (E) unit such as the paraphenylene (P) and fluoro-substituted paraphenylene (PF). The generic structure is similar to that in FIG. 1(b) except that L is a rigid bridging group instead of the flexible group made up by polymethylene or polyoxyethylene chains. Structures of some examples of reactive and nonreactive mesogenic dianhydrides are shown in FIG. 4.

Aromatic Endcappers. The use of thermally reactive 4-ethynylphthalic anhydride (PEPA) and non-reactive phthalic anhydride (PA) as endcapping agents would allow the control of the crosslinking density of L(DPA)-containing TLC-PI products. Thus, when the PE moiety are present in both the backbone and the termini of TLC-PI, higher cross-linking density is expected than when PE is only present in the polymer backbone.

Figure 5:
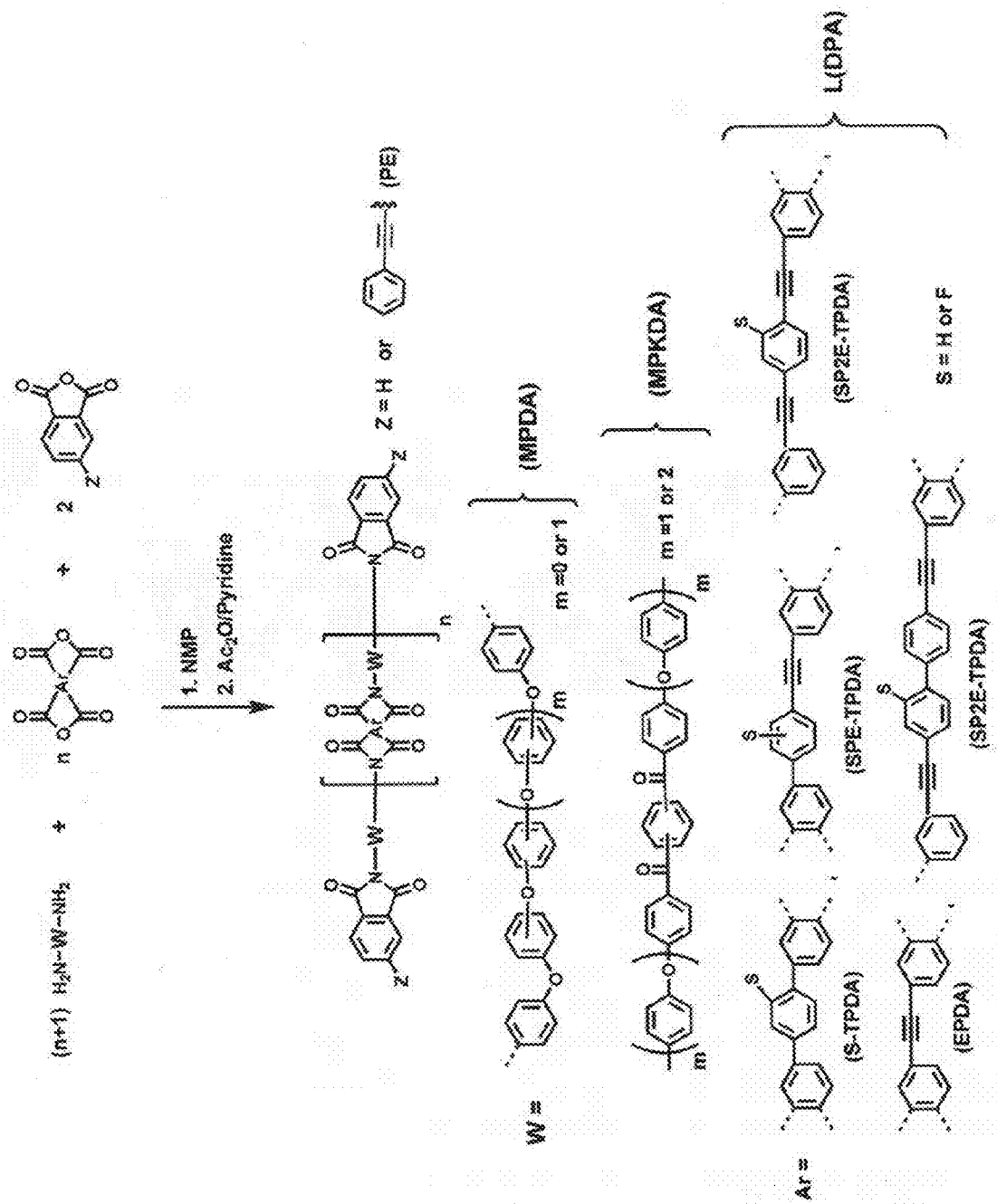
FIG. 5 depicts the general scheme for the syntheses of (i) phthalic anhydride (PA) endcapped and (ii) 4-phenylethynylphthalic anhydride (PEPA)-endcapped LC polyimides (i) PA-[MPDA-L(DPA)]-PA and (ii) PEPA-[MPDA-L(DPA)]-PEPA.

Composition and Preparation of MPDA-Based and MPKDA-based Homopolymers. Accordingly, four series of crosslinkable L(DPA)-containing TLC-PI homopolymers can be designed with the following generic composition and formula: (i) Phthalic anhydride or PA-endcapped series: PA-[MPDA-(R)DPA]-PA; (ii) Phthalic anhydride or PA-endcapped series: PA-[MPKDA-(R)DPA]-PA; (iii) 4-ethynylphthalic anhydride, or PEPA-endcapped series: PEPA-[MPDA-(NR)DPA]-PEPA; (iv) 4-ethynylphthalic anhydride, or PEPA-endcapped series: PEPA-[MPKDA-(NR)DPA]-PEPA Where (R)DPA is thermally reactive mesogenic dianhydrides, and NRDPA is a non-reactive one. The syntheses of phthalimide (PhI) and 4-phenylethynylphthalimide (PEPI)-terminated homopolymers are outlined in the generic scheme depicted in FIG. 5.

Figure 6:
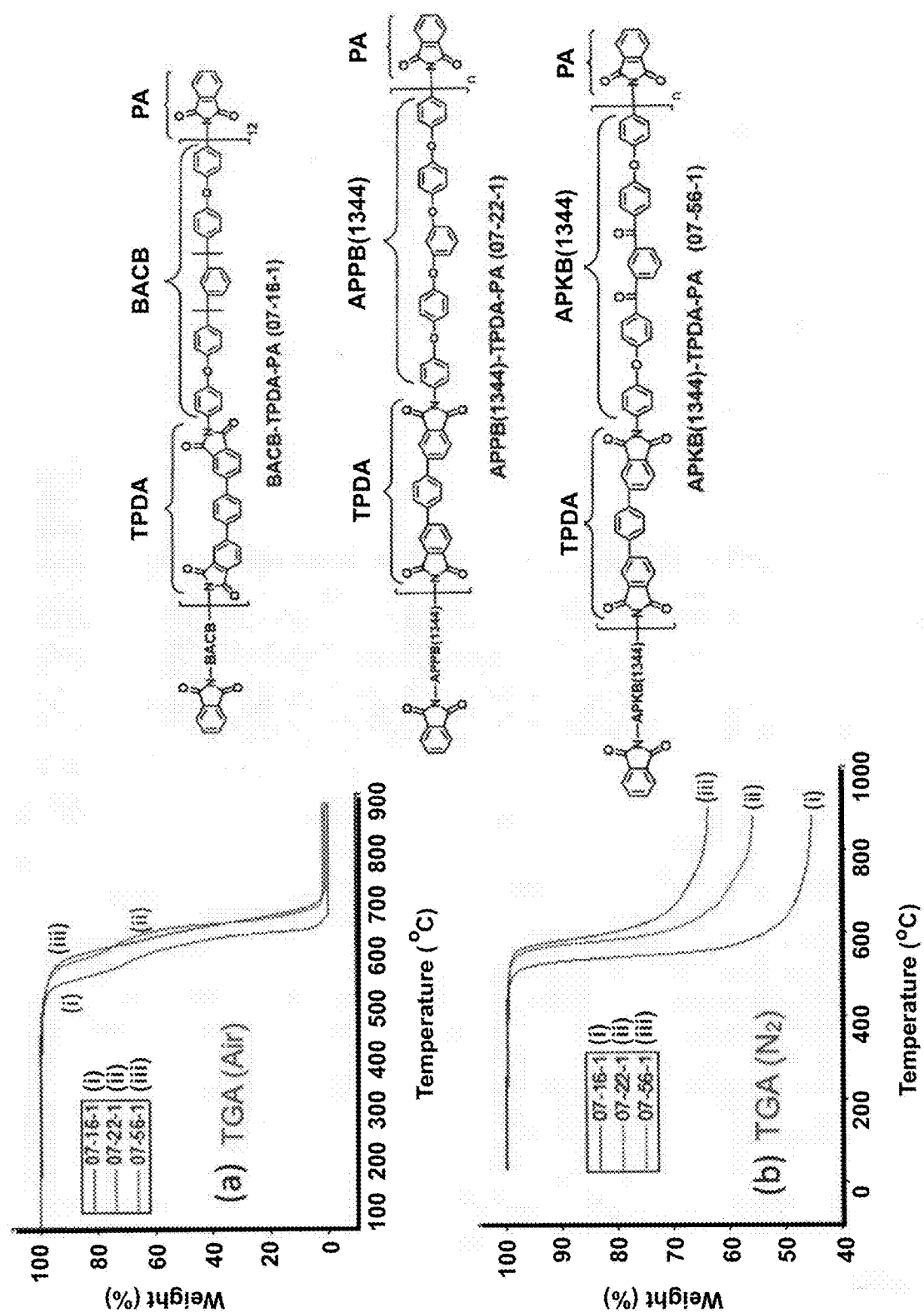
FIG. 6 depicts the composite TGA plots in (a) air and (b) nitrogen atmospheres for the PA-encapped and TPDA-containing (i) BACB-, (ii) APPB(1344)- and (iii) APKB(1344)-based LC-PIs, which have the same degree of polymerization (n=12) and are all thermally noncrosslinkable. The only difference is the nature of moieties in the same positions of their respective polymer backbones: (i) Me$_2$ C< (ii) —O— and (iii) >C=O.

The conceptualization of this new family of liquid crystalline, thermally crosslinkable, and endcapped wholly aromatic imide homopolymers described in the foregoing section has been reduced to practice by the following experimental summary of the polymer synthesis and characterization with respect to thermotropic LC behaviors (POM, complex or dynamic modulus), thermally crosslinking, and thermal & thermostability properties (DSC, TGA). Our main premise for this concept is that MPDA- and MPKDA-based LC-PI should be more heat resistant than BACB-based LC-PI under both inert and oxidizing atmospheres, and it is validated by the comparison of the TGA performance of three representative LC-PIs as depicted in FIG. 6.

Case 1: PA-MPDA-[BPDA-MPDA]$_n$-PA series. Depicted below is the generic structure of phthalic anhydride (PA)-endcapped, low-molecular weight (n=12), polyimide made from 3 3' 4 4'-biphenyltetracarboxylic dianhydride (BPDA) and various of MPDA diamines that have been synthesized:

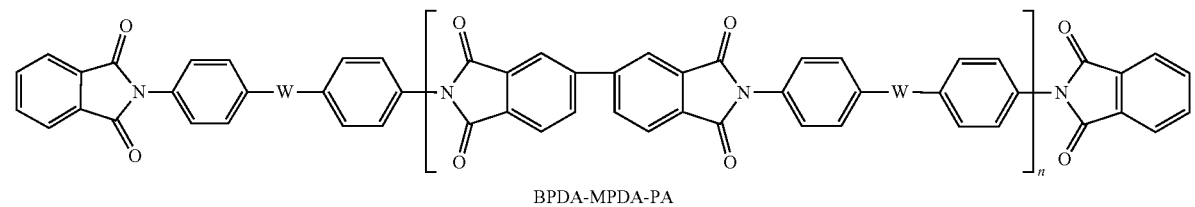

BPDA-MPDA-PA

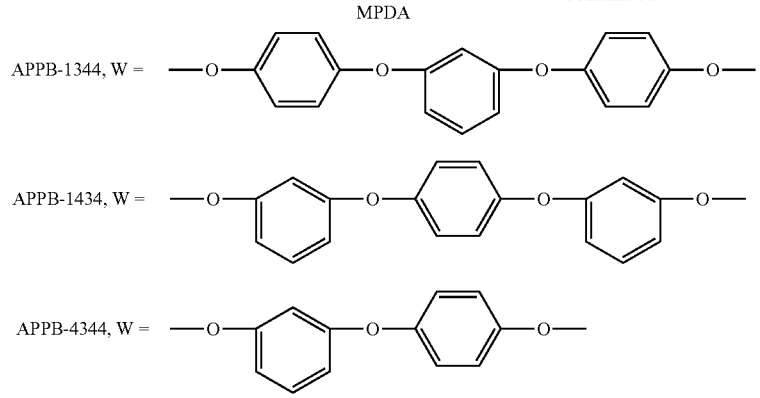

Table 1 summaries the results of thermal characterization and morphological assessment of the PA-[BPDA-MPDA]$_{12}$-PA Series, and indicates that when BPDA is the mesogenic dianhydride and by varying the configuration of the MPDA diamine, it is possible to control the temperature-morphology profile of polyimides to exhibit LC or crystalline or both phases.

TABLE 1

Thermal properties and morphological assignments associated with the observed phase transition for PA-[BPDA-MPDA]$_{12}$-PA Series.

| ID | Diamine | $T_g$ (° C.)[a] | $T_m$ (° C.)[b] | $T_{LC\text{-}iso}$ (° C.)[c] | $T_{iso\text{-}LC}$ (° C.)[d] | $T_{crys}$ (° C.)[e] | Phases[f] |
|---|---|---|---|---|---|---|---|
| 07-22-2 | APPB-1344 | 156.9 | 280.4 317.2 | ND | ND | 240.7 | Crystalline |
| 07-29-2[g] | APPB-1434 | 161.6 | 290.5 (NMP)[h] | N/A | N/A | N/A | Amorphous |
| 07-33-2 | APPA-4344 | 174.8 | 299.4 | ND (>400° C.) | ND (>400° C.) | 272.5 | Crystalline & Liquid crystalline |

Notes:

Thermal transition temperature data from DSC: [a]Glass-transition; [b]melting (first value from heating scan and second value, cooling scan; [c]liquid-crystal (LC) to isotropic (iso) phase transition; [d]isotropic (iso) to liquid-crystal (LC) phase transition; [e]crystallization from cooling scan; [f]Major phase character assigned based on DSC and polarizing optical microscopy (POM) observations; [g]As synthesized; [h]solvent (NMP)-induced crystallization.

Figure 7:
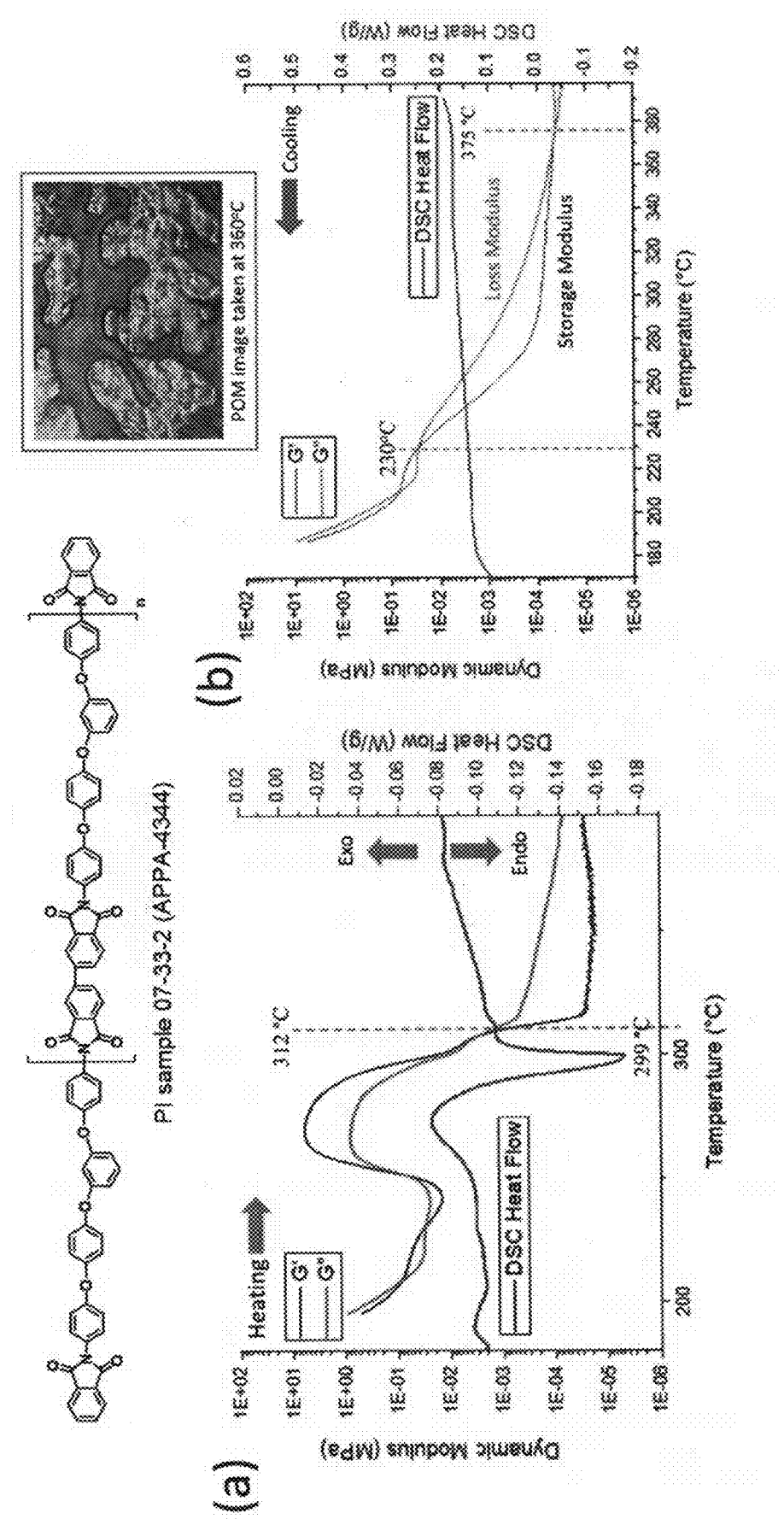
FIG. 7 depicts the experimentally deduced existence of a LC mesophase for the 07-33-2 polyimide sample, PA-[BPDA-APPA(4344)]$_{12}$-PA, as revealed by the combined results of (a) DSC, (b) rheometric analysis and (c) polarized optical microscopy.

FIG. 7 depicts the thermal behavior (DSC) and temperature-dependent shear dynamic modulus of the TLC-PI sample 07-33-2 between 175 and 400° C.: (a) the rheometric curve indicates that when heating above 312° C., the shear loss modulus (G") was higher than storage modulus (G'), and the DSC heating curve indicates that there is an endothermal peak (melting) at 299.4° C. These results implicates that above 312°, the PIs is in liquid state. During the cooling scan from 400° C., a crystallization exotherm (272.5° C.; See Table 1) appears, and the rheometric curves indicates that when cooling to below 375° C., the shear loss modulus begin to surpass the storage modulus down to 230° C. The sample shows strong birefringence under a polarized optical microscope. Based on above information, it is concluded that sample 07-33-2 does exhibit liquid crystalline from 312° C. to 375° C.

Case 2: PA-[TPDA-MPDA]$_{12}$-PA Series. Depicted below is the generic structure of phthalic anhydride (PA)-end-capped, low-molecular weight (n=12), polyimide made from 3 3' 4 4'-biphenyltetracarboxylic dianhydride (BPDA) and various of MPDA diamines that have been synthesized:

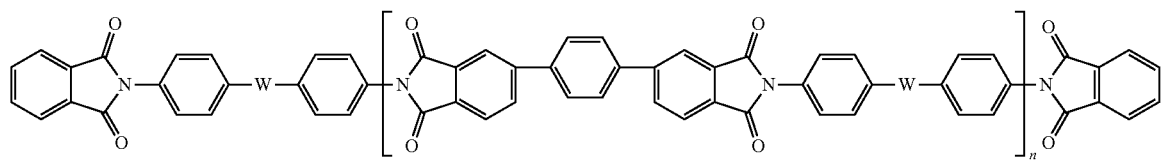

TPDA-MPDA-PA

-continued

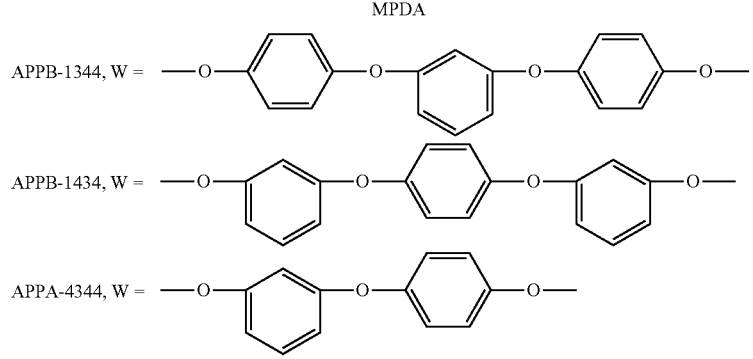

Table 2 summaries the results of thermal characterization and morphological assessment of the PA-[TPDA-MPDA]$_{12}$-PA Series, and indicates that when TPDA is the mesogenic dianhydride and by varying the configuration of the MPDA diamine, it is possible to control the temperature-morphology profile of polyimides to exhibit LC or crystalline or both phases. Because of its higher aspect ratio, TPDA is a stronger mesogen than BPDA as evidenced by its ability to promote liquid crystallinity with the same MPDA diamine (e.g, APPB-1334) in the corresponding polyimide that BPDA is unable to do so.

(G') in this temperature range as the polyimide behaves like a liquid. DSC curve indicates that there is an endothermal transition (crystallization) at 249.5° C. The LC phase of 07-50-1 was assessed by polarized optical microscopy: (a) at 258° C., there was no birefringence but (b) at 248° C., a strong birefringence (bright field) appeared. These results clearly confirm that between 175° C. and 249.5° C., polyimide 07-50-1 is in LC state.

Figure 10:
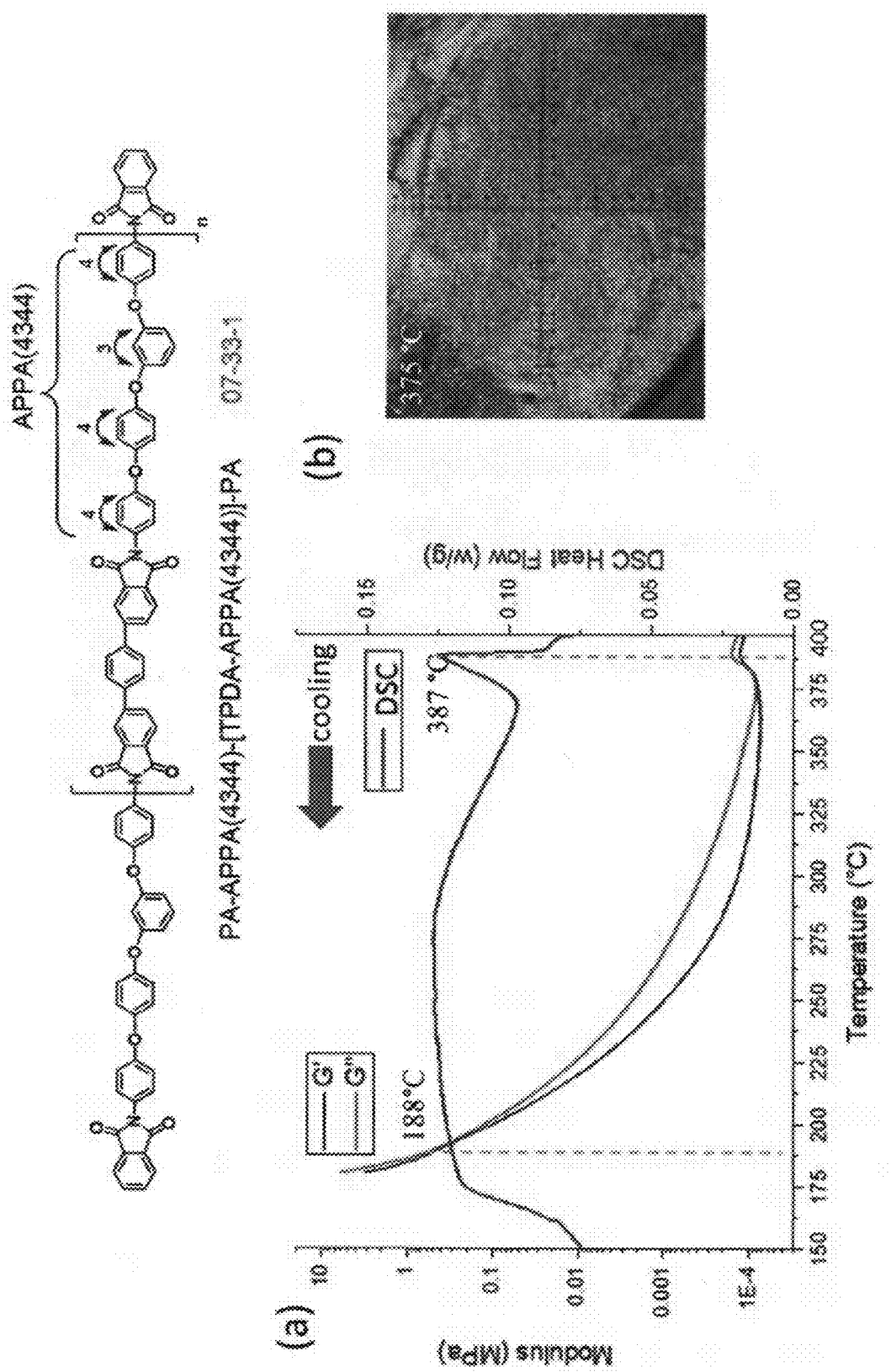
FIG. 10 depicts existence of a LC mesophase for the 07-33-1 polyimide sample revealed by the combined results of (a) DSC, rheometric analysis and (b) polarized optical microscopy.

FIG. 10 depicts the composite plots of the DSC and shear dynamic modulus curves cooling from 400° C. for the 07-33-1 sample: (a) The rheometric (G' and G") curves

TABLE 2

Thermal properties and morphological assignments associated with the observed phase transition for PA-[TPDA-MPDA]$_{12}$-PA series.

| ID | Diamine | $T_g$ (° C.)[a] | $T_m$ (° C.)[b] | $T_{L-i}$ (° C.)[c] | $T_{i-L}$ (° C.)[d] | $T_c$ (° C.)[e] | Phase[f] |
|---|---|---|---|---|---|---|---|
| 07-50-1[g] | APPB-1334 | 150.6 | 254.0 (NMP)[h] | 251.4 | 249.5 | ND | Liquid Crystalline |
| 07-22-1[g] | APPB-1344 | 163.1 | 279.2 (NMP)[h] | 324.1 | 321.9 | ND | Crystalline & Liquid Crystalline |
| 07-29-1 | APPB-1434 | 160.3 | 311.6 | N/A | N/A | 307.5 | Crystalline |
| 07-33-1 | APPA-4344 | 170.9 | 329.4 | 387.3 | 389.0 | 260.0 | Crystalline & Liquid crystalline |

Notes:

Thermal transition temperature data from DSC: [a]Glass-transition; [b]melting (first value from heating scan and second value, cooling scan; [c]liquid-crystal (LC) to isotropic (iso) phase transition; [d]isotropic (iso) to liquid-crystal (LC) phase transition; [e]crystallization from cooling scan; [f]Major phase character assigned based on DSC and polarizing optical microscopy (POM) observations; [g]As synthesized; [h]solvent (NMP)-induced crystallization.

Figure 8:
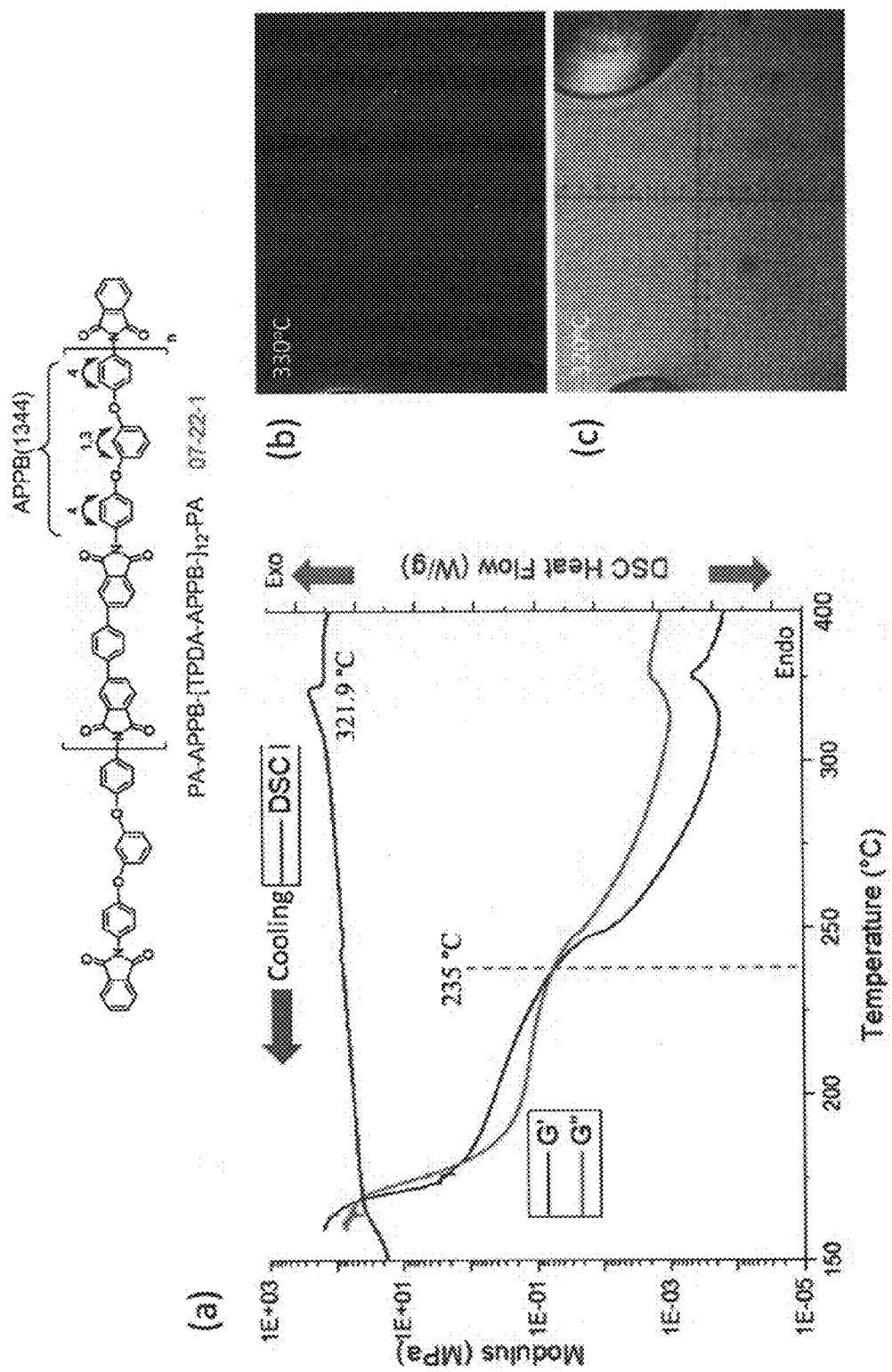
FIG. 8 depicts the experimentally deduced existence of a LC mesophase for the 07-22-1 polyimide sample revealed by the combined results of (a) DSC, rheometric analysis and (b-c) polarized optical microscopy.

FIG. 8 depicts the composite plots of the DSC and shear dynamic modulus curves cooling from 400° C. for the 07-22-1 sample. The rheometric (G' and G") curves reveal that when the temperature is between 250° C. and 400°, the shear loss modulus was greater than storage modulus at this temperature range as the polyimide behaves like a liquid. DSC curve indicates that there is an endothermal transition (crystallization) at 321.9° C. The LC phase of 07-22-1 was assessed by polarized optical microscopy: (a) at 330°, there was no birefringence but (b) at 320° C., a strong birefringence (bright field) appeared. These results clearly indicate that a LC mesophase exists between 250° C. and 320° C.

Figure 9:
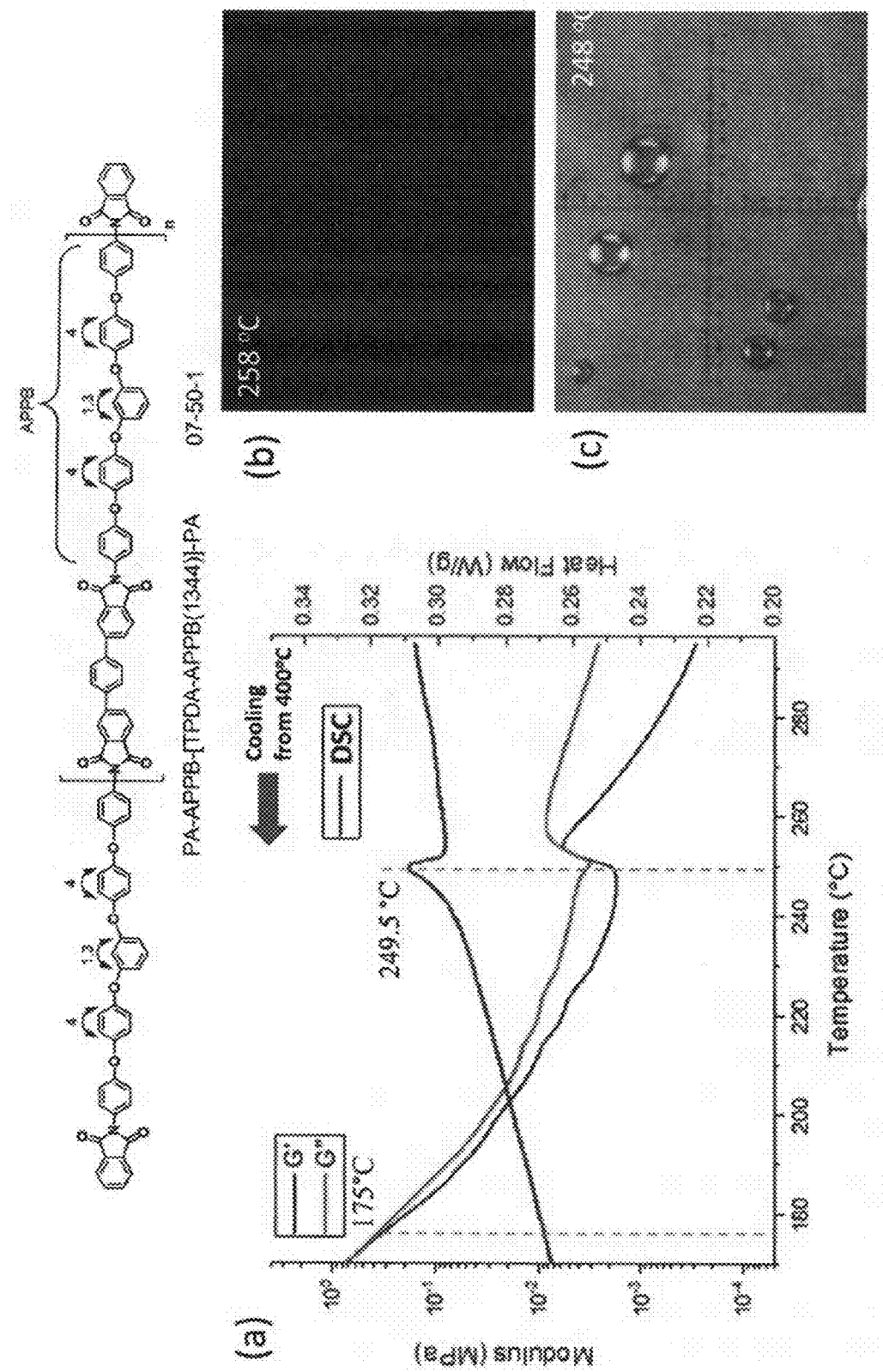
FIG. 9 depicts existence of a LC mesophase for the 07-50-1 polyimide sample revealed by the combined results of (a) DSC, rheometric analysis and (b-c) polarized optical microscopy.

FIG. 9 depicts the composite plots of the DSC and shear dynamic modulus curves cooling from 400° C. for the 07-50-1 sample. The rheometric (G' and G") curves reveal that when the temperature is between 175° C. and 400°, the shear loss modulus (G") was greater than storage modulus (G') in this temperature range as the polyimide behaves like a liquid. DSC curve indicates that there is an endothermal transition (crystallization) at 289° C.; (b) LC mesophase of 07-33-1 was assessed by polarized optical microscopy: at 375° C., there was a strong birefringence. These results clearly confirm that between 329.4° C. and 389° C., polyimide 07-33-1 is in a liquid crystalline state.

Case 3. PA-[(Rigid Dianhydide)-MPKDA]$_{12}$-PA Series. Depicted below is the generic structure of phthalic anhydride (PA)-endcapped, low-molecular weight (n=12), polyimide synthesized from five rigid dianhydrides and four multi-phenoxy ketone dianilines or MPKDA diamine monomers:

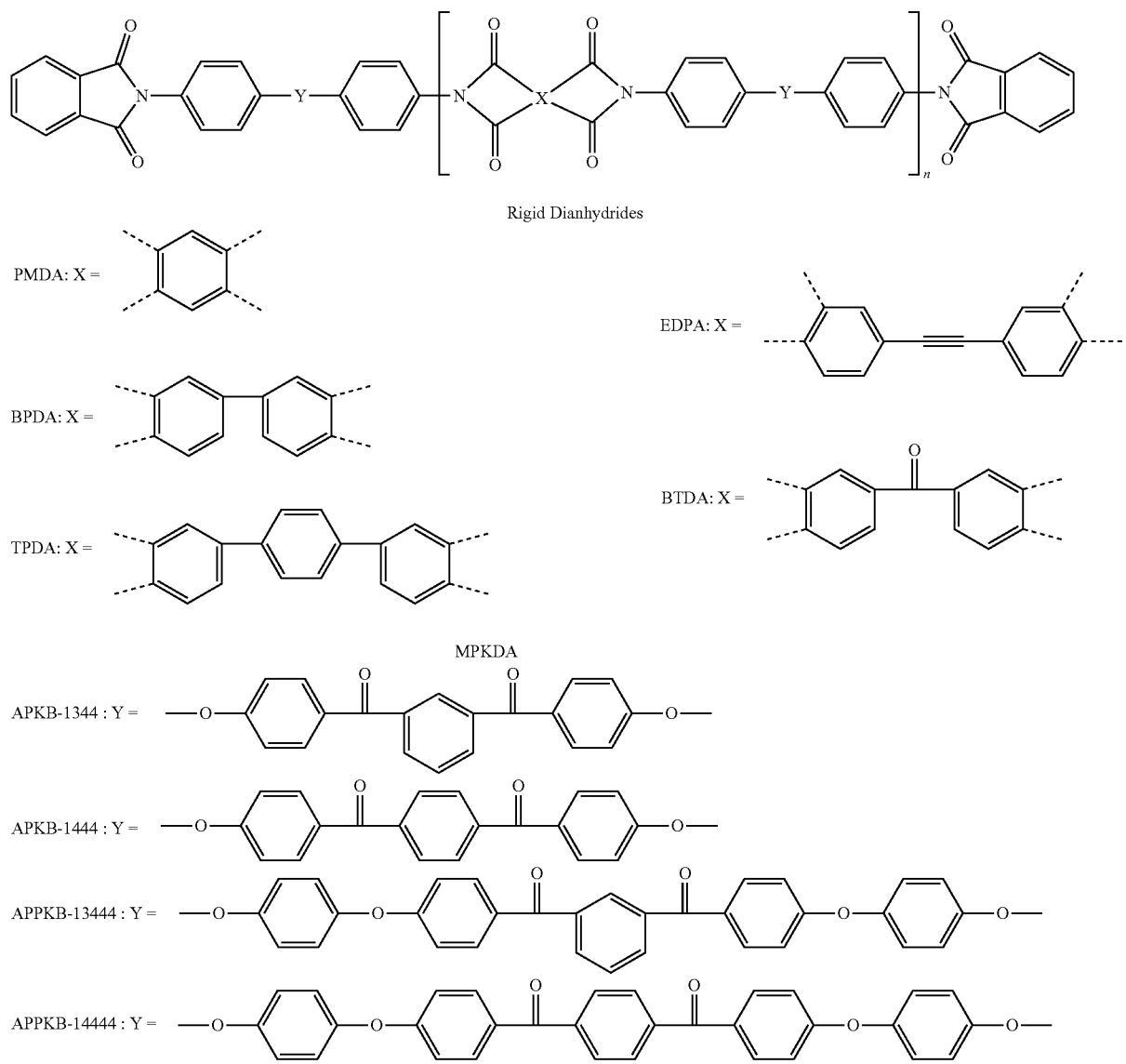

Rigid Dianhydrides

Table 3 summaries the results of thermal characterization and morphological assessment of the PA-[(Rigid Dianhydride)-MPKDA]$_{12}$-PA Series. The results indicate that when TPDA is the mesogenic dianhydride, the replacement of ether unit by the less flexible carbonyl group would not destroy the liquid-crystallinity in TLC polyimides as evidenced by that both TPDA-APPB(1344) and TPDA-APKB (1344) are liquid crystalline. However, the general inclination of having multiple keto-for-ether replacements is toward greater crystallinity and lesser liquid-crystallinity. These results provide some guideline in balancing these structural factors in order to optimize the requirements in processing (liquid-crystallinity) and achieving enhanced properties (crystallinity) for all-aromatic polyimides.

TABLE 3

Thermal properties and morphological assignments associated with the observed phase transition for PA-[(Mesogenic Dianhydride)-MPKDA]$_{12}$-PA Series.

| ID | Dianhydride | Diamine | $T_g$ (° C.) | $T_m$ (° C.) | $T_{LC\text{-}iso}$ (° C.) | $T_{iso\text{-}LC}$ (° C.) | $T_{crys}$ (° C.) | Phase |
|---|---|---|---|---|---|---|---|---|
| 07-56-1 | TPDA | APKB-1344 | 191.30 | 233.8 | 333.6 | 332.6 | ND | Liquid crystalline/Crystalline |
| 07-56-2 | EDPA | APKB-1344 | 192.5 | 310.0 | ND | ND | 267.3 | Crystalline |
| 07-58-2 | TPDA | APKB-1444 | 229.6 | 429.0 | ND | ND | 325.3 | Crystalline |
| 07-60-1 | TPDA | APPKB-14444 | 216.0 | 316.9 | ND | ND | ND | Crystalline from NMP Amorphous from melt |
| 07-60-2 | BDPA | APPKB-14444 | 200.7 | 316.9 366.5 | ND | ND | ND | Crystalline from NMP Amorphous from melt |

TABLE 3-continued

Thermal properties and morphological assignments associated with the observed phase transition for PA-[(Mesogenic Dianhydride)-MPKDA]$_{12}$-PA Series.

| ID | Dianhydride | Diamine | $T_g$ (° C.) | $T_m$ (° C.) | $T_{LC\text{-}iso}$ (° C.) | $T_{iso\text{-}LC}$ (° C.) | $T_{crys}$ (° C.) | Phase |
|---|---|---|---|---|---|---|---|---|
| 07-65-1 | TPDA | APPKB-13444 | 187.9 | 249.0 330.4 | ND | ND | 238.5 | Crystalline |
| 07-65-2 | BPDA | APPKB-13444 | 182.4 | ND | ND | ND | ND | Amorphous |
| 07-68-1 | PMDA | APPKB-13444 | ND | 418.9 | ND | ND | 307.5 | crystalline |
| 07-68-2 | BTDA | APPKB-13444 | 187.0 | 368.0 | ND | ND | 308.5 | crystalline |

Case 4. Thermotropic liquid-crystalline, crosslinkable, and aromatically-endcapped all-aromatic polyimides. Conceptually, four series of crosslinkable L(DPA)-containing TLC-PI homopolymers can be designed with the following generic composition and formula: (i) Phthalic anhydride or PA-endcapped series: PA-[MPDA-(R)DPA]-PA; (ii) Phthalic anhydride or PA-endcapped series: PA-[MPKDA-(R)DPA]-PA; (iii) 4-ethynylphthalic anhydride, or PEPA-endcapped series: PEPA-[MPDA-(NR)DPA]-PEPA; (iv) 4-ethynylphthalic anhydride, or PEPA-endcapped series: PEPA-[MPKDA-(NR)DPA]-PEPA where (R)DPA is thermally reactive mesogenic dianhydrides, and NRDPA is a non-reactive one. We have accomplished the proof-of-concept work for series (i) and (iii) and would expect similar outcomes for series (ii) and (iv).

Depicted below is the generic structure for both the phthalic anhydride (PA)- and 4-phenylethynylphthalic anhydride (PEPA)-endcapped, low-molecular weight (n=12), polyimides with backbone made from mesogenic dianhydrides, L(DPA) and APPB-1334 diamines that have been synthesized and characterized as proof-of-concept examples. Our concept of liquid crystallinity and crosslinkability are supported by the thermal property data (DSC) and morphological phase assignment via temperature-variable POM; data summarized in Tables 4 and 5, and illustrated by FIG. 9.

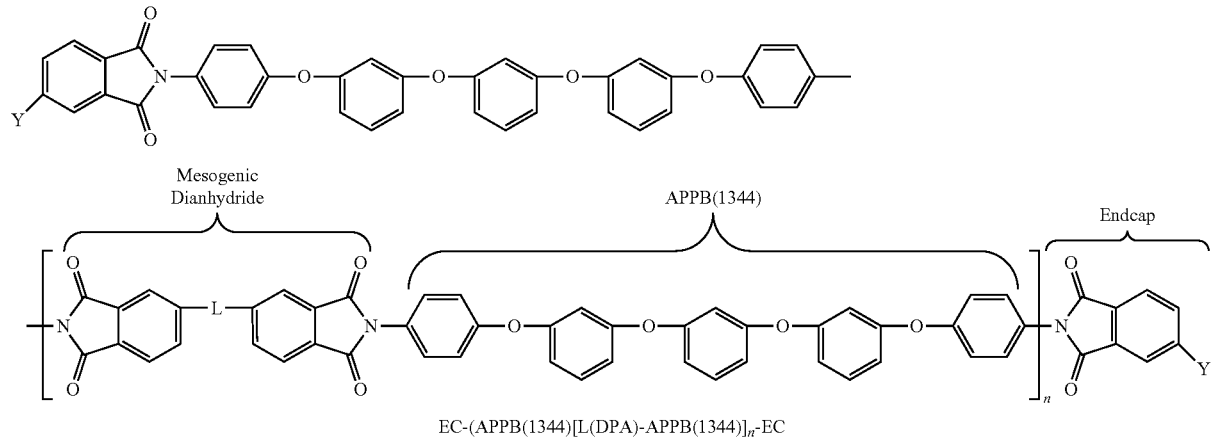

EC-(APPB(1344)[L(DPA)-APPB(1344)]$_n$-EC

TABLE 4

Thermal properties and morphological assignments associated with the observed phase transition (before crosslinking reaction) for thermotropic liquid-crystalline, crosslinkable, and aromatic-endcapped all-aromatic polyimide series, EC-APPB(1334)[(L(DPA)-APPB(1334)]$_n$-EC.

| ID | Dianhydride L(DPA) | End Cap EC | $T_g$ (° C.)[a] | $T_m$ (° C.)[b] | $T_{LC-iso}$ (° C.)[c] | $T_{iso-LC}$ (° C.)[d] | $T_{crys}$ (° C.)[e] | Phase |
|---|---|---|---|---|---|---|---|---|
| 07-17-2 | TPDA | PA | 154.1 | ND | 272.4 | 266.2 | ND | Crystalline & Liquid crystalline |
| 07-46-1 | EDPA | PA | 139.5 | 284.9 | ND | ND | 266.6 | Crystalline |
| 07-46-2 | EDPA | PEPA | 140.0 | 288.5 | ND | ND | 270.2 | Crystalline |
| 08-71-1 | PEDPA | PEPA | 140.6 | 265.3 | ND | 244.0 | 227.4 | Liquid crystalline |
| 07-47-2 | 1,4-P2EPA | PEPA | 143.4 | 250.0 305.0 | ND | ND | 197.6 258.8 | Crystalline |

Notes:
Thermal transition temperature data from DSC: [a]Glass-transition; [b]melting (first value from heating scan and second value, cooling scan; [c]liquid-crystal (LC) to isotropic (iso) phase transition; [d]isotropic (iso) to liquid-crystal (LC) phase transition; [e]crystallization from cooling scan; f. Major phase character assigned based on DSC and polarized optical microscopy (POM) observations.

For the PA-endcapped series, thermal crosslinking reaction is limited to between the backbone arylethynyl groups and could occur in interchain or intrachain mode. For the PEPA-endcapped series, thermal crosslinking can occur between the multiple backbone arylethynyl units or between backbone arylethynyl units and PEPA endgroups. The DSC data in Table 5 indicate that both types of crosslinking reaction would start at temperatures well over 300° C., which is considerably over the LC mesophase temperature (272.4° C. for PA-TPDA-APPB1334, ID 07-17-2 and 166° C. for PEPA-PEDPA-APPB1334, ID 07-47-1; see Table 2).

TABLE 5

Thermal crosslinking temperatures and morphological assignments associated with the observed phase transition (after crosslinking reaction) for thermotropic liquid-crystalline, crosslinkable, and aromatic-endcapped all-aromatic polyimide series, EC-APPB(1334)[(L(DPA)-APPB(1334)]$_n$-EC.

| ID | Dianhydride L(DPA) | End Cap EC | $T_{onset}$ (° C.) | $T_{peak}$ (° C.) | Post Cure $T_g$ (° C.)* | Post Cure $T_m$ (° C.) |
|---|---|---|---|---|---|---|
| 07-46-1 | EDPA | PA | 353.4 | 423.5 | Not Detected (DSC) | ND (DSC) |
| 07-46-2 | EDPA | PEPA | 350.9 | 418.9 | Not Detected (DSC) | ND (DSC) |
| 08-71-1 | PEDPA | PEPA | 326.2 | 441.5 | Not Detected (DSC) | ND (DSC) |
| 07-47-2 | 1,4-P2EDPA | PEPA | 344.0 | 409.1 | Not Detected (DSC) | ND (DSC) |

Figure 11:
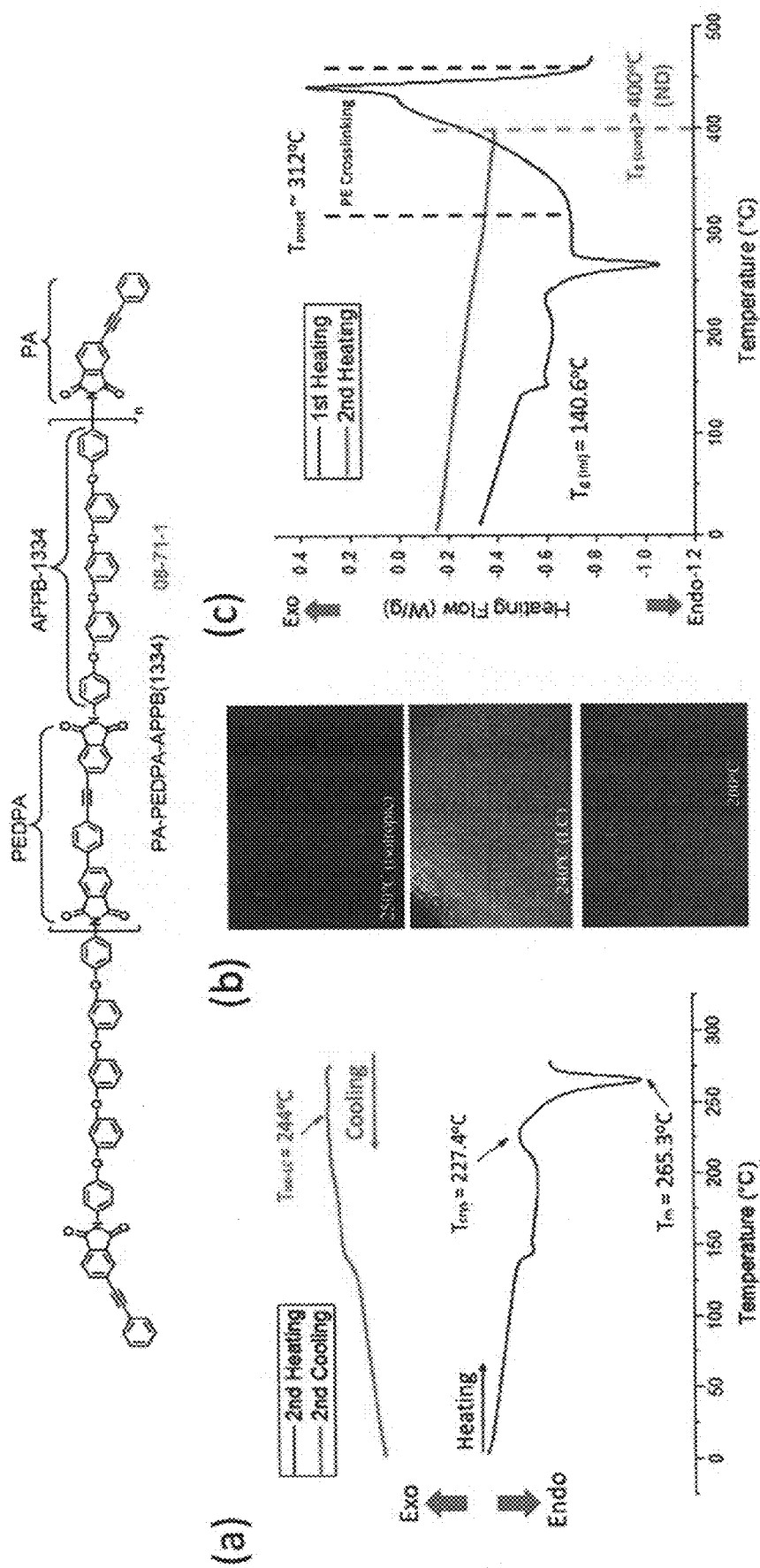
FIG. 11 depicts (a) DSC scans in heating to (black) and cooling from (red) 280° C. of sample 08-71-1 to detect phase transitions; (b) POM images of cooling 08-71-1 melt from 280° C. and taken at different temperatures, indicating liquid crystalline phase ~240-250° C. before phenylethynyl (PE) crosslinking occurring curing at temperature above 310° C. and (c) Initial DSC scan of 08-71-1 to 500° C. to detect phase transitions and PE crosslinking reaction and rescan of the cured sample to 400° C.

FIGS. 11(a) and (c) depict the DSC trace for polyimide sample 08-71-1 as an example for series III. It is revealed that before curing, the polyimide exhibits multiple phase transitions below 310° C. (initial glass transition, crystallization, and melting). Curing process would happen above 310° C., i.e. after essentially completed melting. The second heating scan DSC conducted for the cured sample shows that there is no thermal transition up to 400° C., indicating the cured sample is practically an isotropic solid with glass transition beyond 400° C. FIG. 11(b) depicts the POM images of 08-71-1 taken at different temperatures, indicative of isotropic phase above 250° C. and liquid crystalline state ~244-250° C. in agreement with DSC data in FIG. 11(a).

Case 5. Liquid crystallinity and Crosslinkability of PA-[(Rigid Dianhydride)-MPKDA]$_{12}$-PA Series Containing Multiple aromatic keto units.

Table 6 summaries and compares the results of thermal characterization and morphological assessment of the PA-[(Rigid Dianhydride)-MPKDA]$_{12}$-PA Series. The results indicate that when the thermally nonreactive TPDA or crosslinkabe PEDPA is the mesogenic dianhydride, the replacement of isopropyl or ether unit by the less flexible carbonyl group would not destroy the liquid-crystallinity in TLC polyimides as evidenced by the examples of TPDA-APPB(1344) and PEDPA-APKB(1344). However, the general inclination of having multiple keto-for-ether replacements is toward greater crystallinity and lesser liquid-crystallinity. These results provide some guideline in balancing these structural factors in order to optimize the requirements in processing (liquid-crystallinity) and achieving enhanced properties (crystallinity) for all-aromatic polyimides, especially in combination with the presence of keto-linker in the dianhydride component. However, the presence of high crystallinity that are heat-resistance (300-400° C.) can enhance mechanical properties and chemical and solvent resistance under ambient stand-down conditions and serve as relatively strong, noncovalent crosslinking to maintain structural integrity at moderately high temperature environment.

Table 6. Comparison of thermal properties and morphological assessment of selected PA-[(Rigid Dianhydride)-MPKDA]$_{12}$-PA examples to highlight the collective effect of having multiple aromatic keto units on liquid crystallinity of all-aromatic polyimides.

| ID | Dianhydride L = | H₂N-⌬-Y-⌬-NH₂ | $T_g$ (°C.) | $T_u$ (°C.) | $T_{LC\text{-}iso}$ (°C.) | $T_{iso\text{-}LC}$ (°C.) | $T_{crys}$ (°C.) | Phase |
|---|---|---|---|---|---|---|---|---|
| 07-56-1 | (TPDA) | APKB-1344 | 191.30 | 233.8 (NMP) | 333.6 | 332.6 | ND | Liquid crystalline |
| 08-71-2 | (PEDPA) | APKB-1344 | 180.0 | 277.9 | ND | ND | ND | Liquid Crystalline & Crystalline |
| 07-68-2 | (BTDA) | APPKB-13444 | 187.0 | 368.0 | ND | ND | 308.5 | Crystallinity |

APKB-1344: Y = —O-⌬-C(O)-⌬-C(O)-⌬-O—

APPKB-13444: Y = —O-⌬-O-⌬-C(O)-⌬-C(O)-⌬-O-⌬-O—

Figure 12:
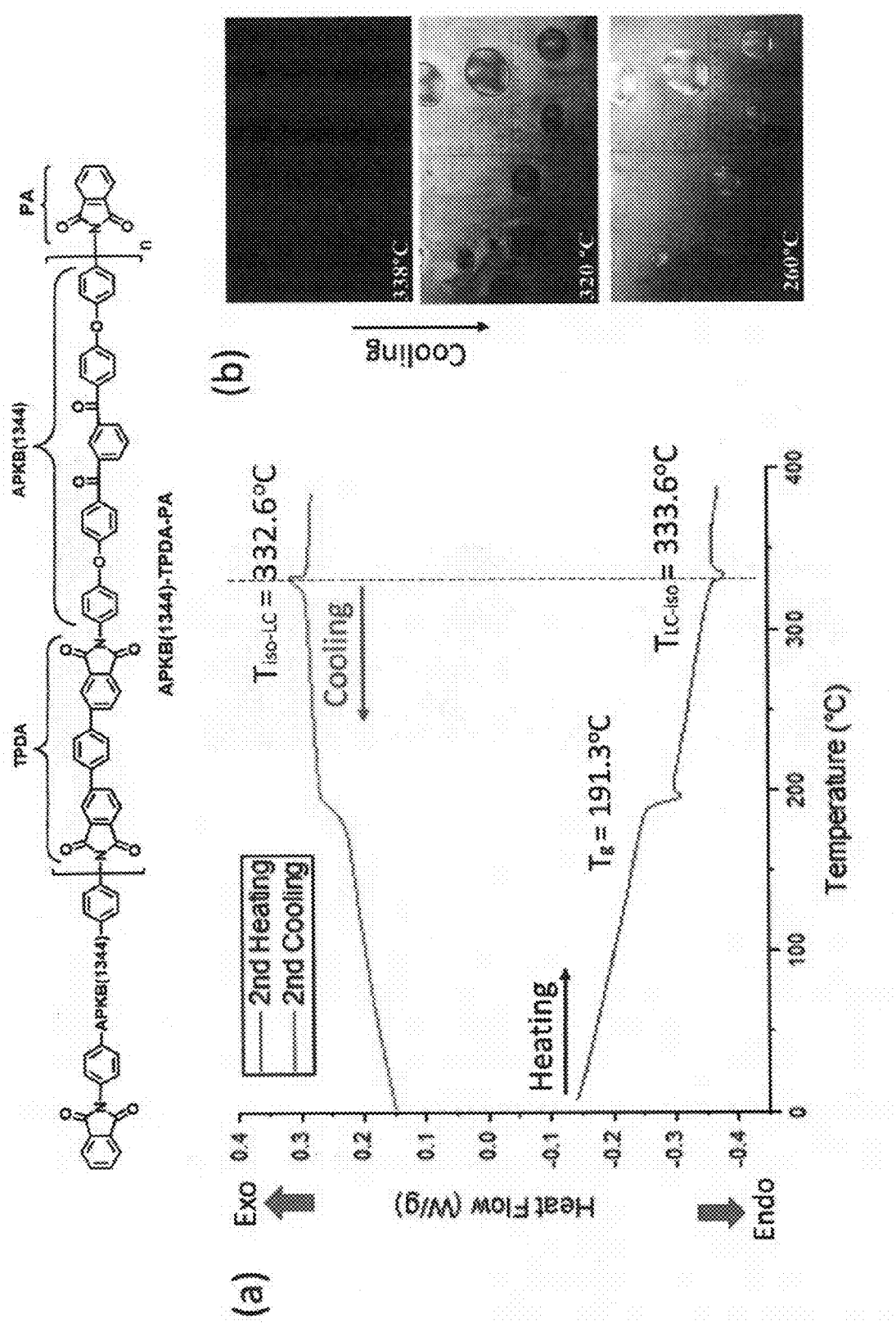
FIG. 12 depicts (a) DSC second scans of phthalic anhydride (PA)-endcapped APKB(1344-TPDA (07-56-1), heating to and cooling from 400° C. to reveal glass transition and liquid crystalline (LC)/isotropic (iso) transition in both heat-flow directions; (b) POM pictures of 07-56-1 at different temperature while cooling from isotropic phase, temperatures from top: 338° C., 320° C. and 260° C.

FIG. 12 depicts (a) DSC second scans of phthalic anhydride (PA)-endcapped APKB(1344-TPDA (07-56-1), heating to and cooling from 400° C. to reveal glass transition and liquid crystalline (LC)/isotropic (iso) transition in both heat-flow directions; (b) POM pictures of 07-56-1 at different temperature while cooling from isotropic phase, temperatures from top: 338° C., 320° C. and 260° C.

Figure 13:
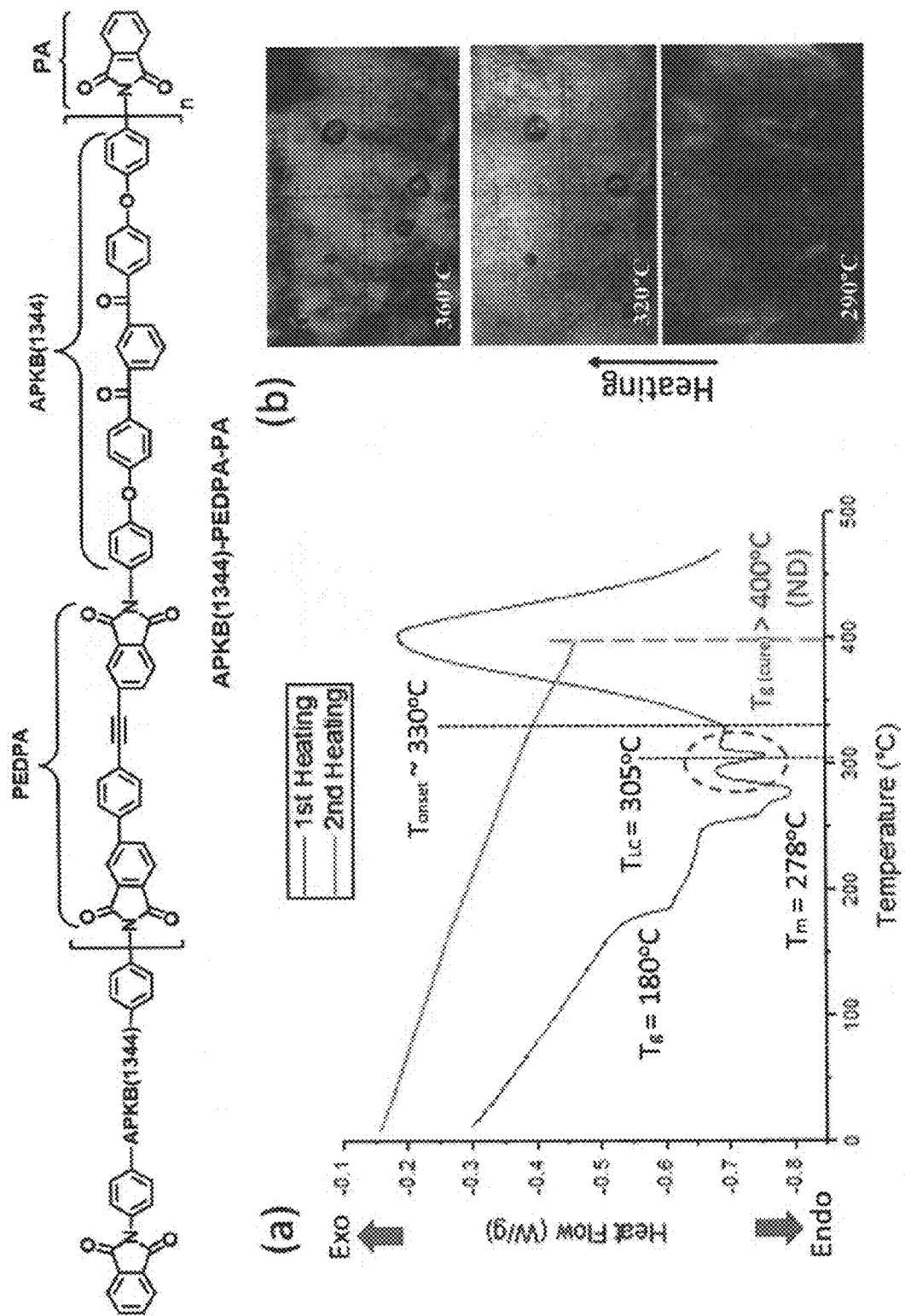
FIG. 13 depicts (a) first DSC heating scan of phthalic anhydride (PA)-endcapped APKB(1344)-PEDA (08-71-2) to 475° C., revealing the thermal events of glass transition, melting, and phenylethynyl (PE) crosslinking, and second DSC heating scan to 400° C. that shows no glass transition present in the cured product of 08-71-2 sample, (b) POM images of 08-71-2 taken at temperatures (from bottom to top: 290° C., 320° C., 360° C.) while heating from crystalline phase and confirming LC phase detected in DSC scan.

FIG. 13 depicts (a) first DSC heating scan of phthalic anhydride (PA)-endcapped APKB(1344)-PEDA (08-71-2) to 475° C., revealing the thermal events of glass transition, melting, and phenylethynyl (PE) crosslinking, and second DSC heating scan to 400° C. that shows no glass transition present in the cured product of 08-71-2 sample, (b) POM images of 08-71-2 taken at temperatures (from bottom to top: 290° C., 320° C., 360° C.) while heating from crystalline phase and confirming LC phase detected in DSC scan.

Thermal Chemistry of Phenylethynyl Group. According to Connell, Smith, and Hergenrother, Journal of Macromolecular Science, Reviews in Macromolecular Chemistry and Physics 2000, vol. C40, pp. 207-230, the thermal reaction of phenylethynyl (PE) groups when attached to the chain-ends or side-chains of a linear oligomer or polymer, it is thermochemically stable up to 300° C. When the PE-containing units are more spatially constrained (i.e. with both ends tied) in the main chain of the polymer than their counterparts at the chain-ends or side-chains (i.e. each with one end free of constraint), their resistance to thermal crosslinking is significantly increased with their reactivity concomitantly delayed to higher temperatures (≥350° C.), as illustrated by the work of T. Takeichi and M. Tanikawa, Journal of Polymer Science Part A: Polymer Chemistry 1996, vol. 34, pp. 2205-2211. As shown in Table 8 (associated with Example 18), the onset temperature of the internal ethynyl groups in LDPA, such as EDPA incorporated in an all-aromatic polyimide backbone, ranges from 350-390° C.

Figure 14:
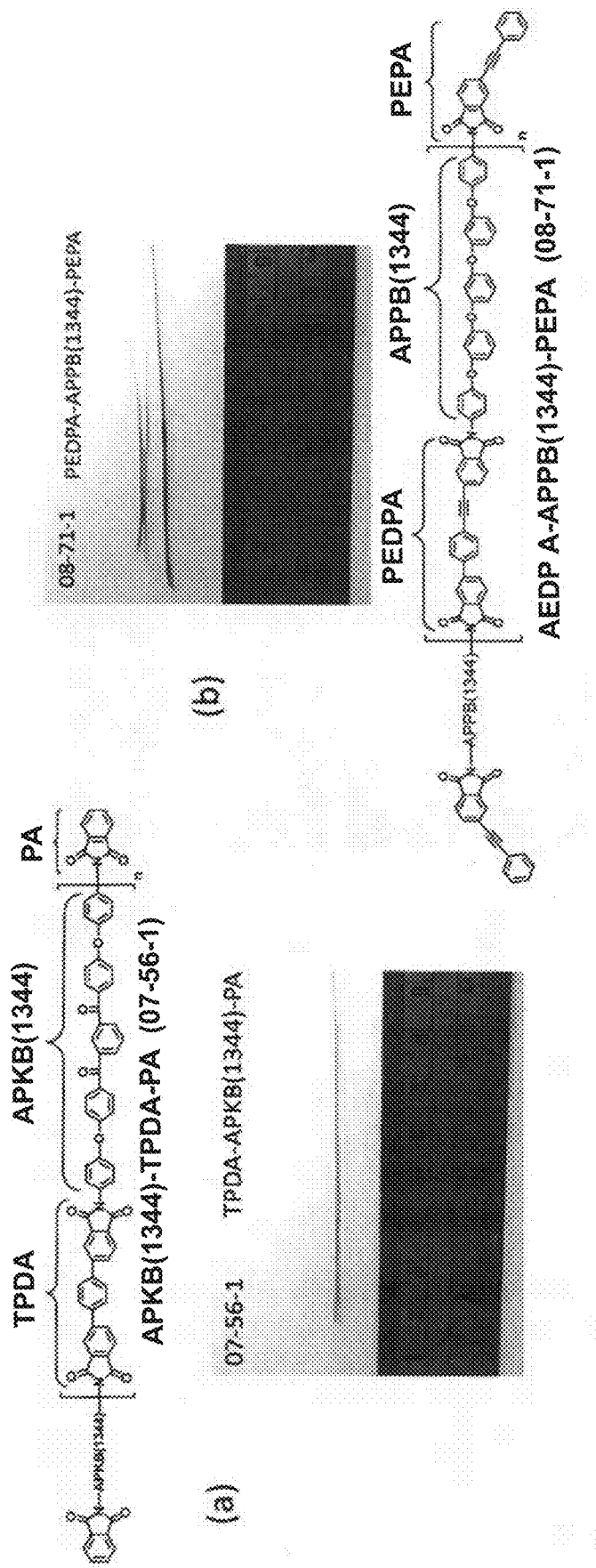
FIG. 14 depicts the pulled fibers from the polymer melts of PA-endcapped TPDA-APKB(1344)-PA (07-56-1) at 310-330° C. and PEPA-endcapped PEDPA-APPB(1344)-PEPA (08-71-1) at 260-280° C.

Fiber Extrusion. 3D printing of interest is an extrusion-type polymer processing. Thus, the extrudability of both PA- and PEPA endcapped thermotropic MPDA-L(DPA and MPKDA-L(DPA) homopolyimides is exemplified by fiber-forming capability of PA-endcapped TPDA-APKB(1344)-PA (07-56-1) and PEPA-endcapped PEDPA-APPB(1344)-PEPA (08-71-1) by respectively having fibers, as depicted in FIG. 14, pulled from their melts. Qualitatively, the fibers are mechanically robust as they were pulled in their LC phases, and for PEPA-fiber sample (08-71-1) also below the temperature (>>300° C.) at which the phenylethynyl groups are expected to crosslink. For TPDA-APKB(1344)-PA (07-56-1), its strong crystallinity at room temperature has led to relatively high stiffness.

All-Aromatic Liquid-Crystalline Homo-Polyimides with Aromatic Endgroups and Processes of Making and Using Same For purposes of this specification, headings are not considered paragraphs. In this paragraph, Applicants disclose polyimide having the following formula:

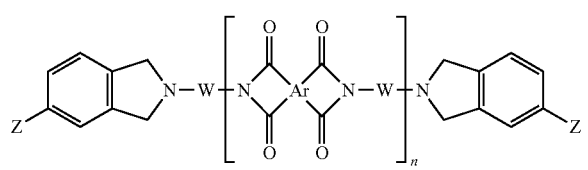

wherein:
n is an integer from 2 to 100, preferably n is an integer of 4 to 20, more preferably n is an integer of 6 to 18;
each W is identical and is selected from one of the following formula:

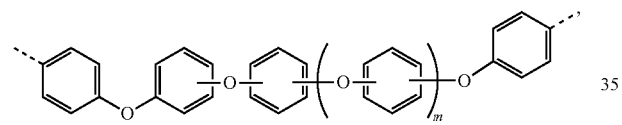

where m is 0 or 1

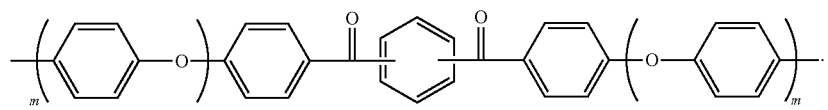

where each m is independently 1 or 2.

Ar has one of the following formula wherein R is H Me, OMe, CN or F, preferably R is H, Me, OMe or F, more preferably R is H, Me or F, most preferably R is H or F: wherein R is H Me, OMe, CN or F, preferably R is H, Me, OMe or F, more preferably R is H, Me or F, most preferably R is H or F,

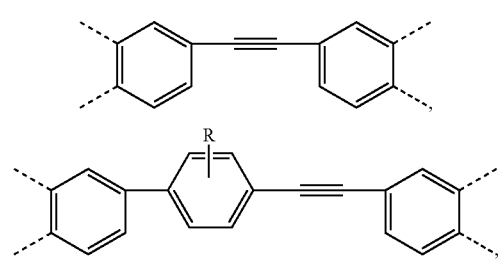

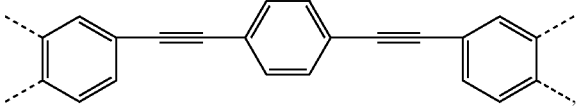

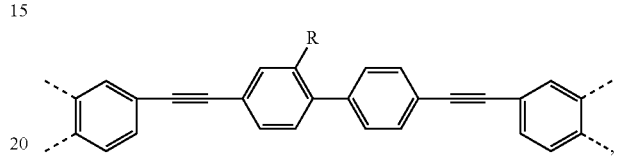

each Z is independently hydrogen or has the following structure

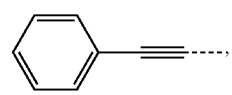

preferably, each Z has the following structure

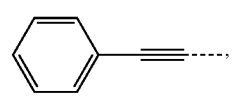

In this paragraph, Applicants disclose the polyimide of the previous paragraph wherein Ar has one of the following formula:

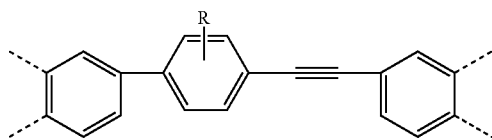

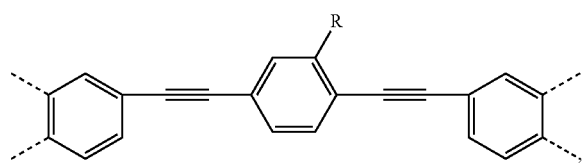

In this paragraph, Applicants disclose a molecule having a formula selected from one of the following formulae:

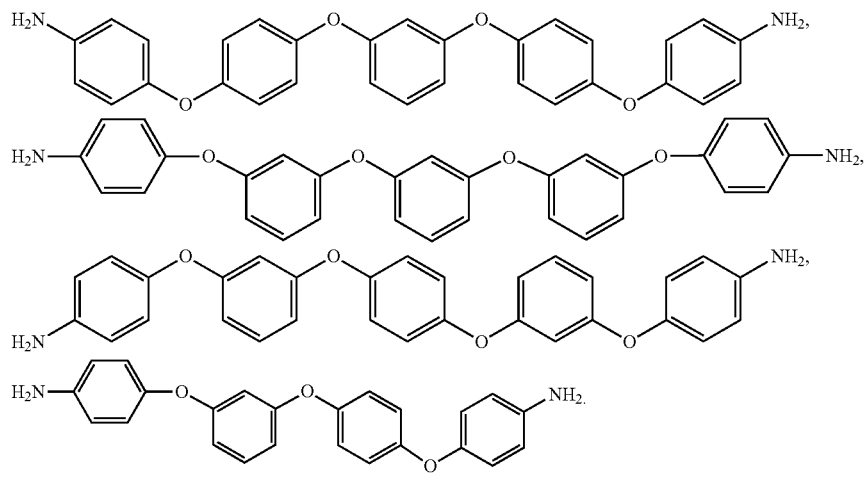

In this paragraph, Applicants disclose a process of making an arylether diamine, said process comprising coupling an aminophenoxyphenol using a dihalobenzene or an aminophenoxyarylhalide, preferably said dihalobenzene is dibromobenzene or diodobenzene in either meta or ortho orientation, and said aminophenoxyarylhalide is aminophenoxyarylbromide or aminophenoxyaryliodide, preferably said amino phenoxyphenol with mixed para-meta substitution patterns has one of the following formulae:

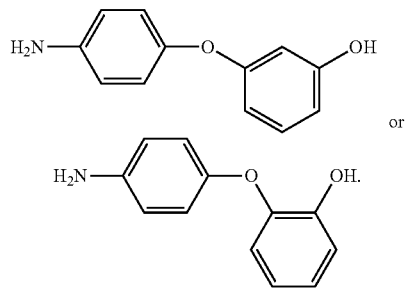

While the conventional thinking with respect to liquid-crystalline polymer systems enabled by semi-flexible linkage comprised of oligomeric phenoxy chain, the substitution patterns of the ethers are in all-para. As exemplified by the work of Dingesman et al. (Guan, Q.; Norder, B.; Chu, L.; Besseling, N. A. M.; Picken, S. J.; Dingemans, T. J. All-Aromatic (AB)n-Multiblock Copolymers via Simple One-Step Melt Condensation Chemistry. Macromolecules 2016, 49, 8549-8562), the liquid-crystallinity phases in these polymers typically occur at high temperature (>>300° C.) that are impractical for processing and fabrication conditions. In addition, in our work, there is evidence for our polyimides that given a certain mesogenic dianhydride component, all-para multi-phenoxy linkage does not necessary lead to liquid-crystalline character in the resulting polyimide, and on the other hand, a balanced mix of para and meta phenoxy in the linkage can lead to a liquid crystalline polyimide

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Synthesis of MPDA and MPKDA Diamine Monomers

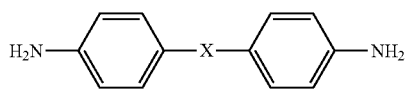

| X | Code |
|---|---|
| 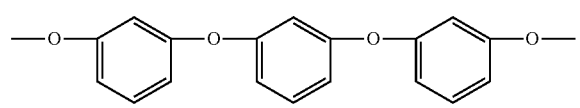 | APPB-1334 |
| 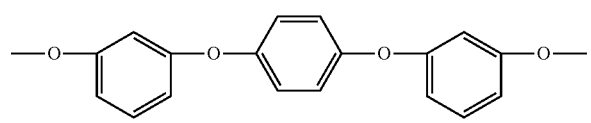 | APPB-1434 |

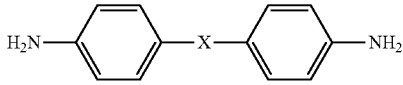

| X | Code |
|---|---|
|  | APPB-1344 |
| 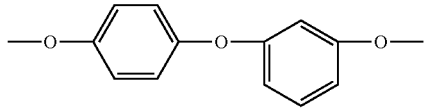 | APPA-4344 |
| 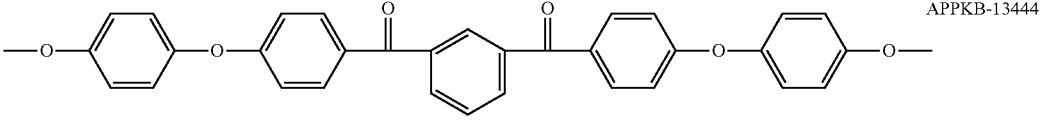 | APPKB-13444 |

Example 1 Synthesis 3-(4-nitrophenoxy)phenol. To 300 mL round bottle flask, equipped with magnetic stir bar, nitrogen inlet, outlet 13.2 g (0.12 mmol) resorcinol, 10.0 g (0.25 mol) of sodium hydroxide, were charge. After vacuum-back-filled with nitrogen for three times, 50 mL water and 40 mL dimethyl sulfoxide were charged. The mixture as heated in an oil bath to 50° C. To the mixture, 14.1 g (0.10 mol) 4-fluoro-1-nitrobenzene in 10 mL dimethyl sulfoxide was added within 6 hours. After additional the mixture was held at 50° C. for 16 hours. After cooled to room temperature, the mixture was poured into 300 mL water. Solids were removed via filtration. The filtrate was neutralized by concentrate hydrochloric acid until pH of solution to 6. The solution was extraction with ethyl acetate for 3 time. The combined ethyl acetate phase was washed with 5% potassium carbonate solution, then water until TLC show there is no more resorcinol. The ethyl acetate layer was dried out anhydrous magnesium sulfate. After ethyl acetate was removed, the product was obtained as 13.5 g yellow crystals, m.p. 90.0-93.0° C. 58.3% isolated yield. $^1$H NMR (CDCl$_3$): $\delta$=8.19-8.21 (d, J=7.6 Hz, 2H), 7.25-7.30 (m, 1H), 7.02-7.04 (d, J=8.4 Hz, 2H), 6.72-6.74 (d, J=8.4 Hz, 1H), 6.64-6.66 (d, J=7.6 Hz, 1H), 6.60 (s, 1H), 5.46 (s, 1H).

Example 2. Synthesis of Synthesis of 1,3-bis[3-(4-nitrophenoxy)phenoxy]benzene. To a 300 mL round bottom flask equipped with stir bar, nitrogen inlet and condenser, 8.57 g (25.2 mmol) 3-(4-nitrophenoxy)-1-iodo-benzene, 1.32 (12.0 mmol) resorcinol, 0.229 (1.2 mmol) copper iodide, 0.295 g (2.4 mmol) 2-picolinic acid, 10.19 g (48.0 mmol) potassium phosphate were charged. After vacuum-back-filled with nitrogen for three times, 40 mL dimethylsulfoxide was charged. The mixture was heated to 95° C. in an oil bath and held for 36 hours. After cooled to room temperature, the mixture was poured into water, and extracted with ethyl acetate. The ethyl acetate layer was washed with D-ionized water, and dried over anhydrous magnesium sulfate. After ethyl acetate was removed, the crude product was obtained as yellow oil. The crude product was further purified by silica gel chromatography, heptane/toluene 1:1 as eluent. 4.20 grams of product was obtained as yellow oil, 65.2% isolated yield. $^1$H NMR (CDCl$_3$): $\delta$=8.20-8.22 (m, 4H), 7.32-7.42 (m, 4H), 7.02-7.04 (m, 4H), 6.72-6.93 (m, 8H).

Example 3 Synthesis of 1,3-bis[3-(4-aminophenoxy)phenoxy]benzene (APB-1334). To a 100 mL round bottom flask equipped with stir bar, nitrogen inlet 4.20 (7.83 mmol) 1,3-bis[3-(4-nitrophenoxy)phenoxy]benzene 4.94 (78.30 mmol) ammonium formate, 0.16 g 10% palladium on carbon. After vacuum-back-filled with nitrogen for three times, 40 mL methanol and 20 mL tetrahydrofuran were charged. The mixture stir at room temperature for 36 hours. The mixture was filtrated. The filtrate was concentrated under reduce pressure to give crude product. The crude product was further purified by silica gel chromatography, ethyl acetate/toluene 1:1 as eluent. 1.92 grams of product was obtained as yellow oil, 50.9% isolated yield. $^1$H NMR (CDCl$_3$): $\delta$=7.26-7.25 (m, 4H), 6.85-6.87 (d, J=8.8 Hz, 4H), 6.61-6.73 (m, 12H), 3.57 (s, 4H).

Example 4 Synthesis of 3-(4-aminophenoxy)phenol. To a 500 mL round bottom flask equipped with stir bar, nitrogen inlet, 23.1 g (100.0 mmol) 3-(4-nitrophenoxy)phenol, 75.67 g (1.20 mol) ammonium formate, were charged. After vacuum-back-filled with nitrogen for three times, 0.5 g 10% palladium on carbon and 300 mL methanol were charged. The mixture was stirred at room temperature for 3 hours. The solid was washed with ethyl acetate. The methanol and ethyl acetate was removed under reduced pressure. The crude product was washed de-ionized water, air convection dried. 19.3 grams of product was obtained as light yellow crystals, 96% isolated yield, m.p 174.8-178.4° C. $^1$H NMR (CD$_2$C$_{12}$): $\delta$=7.10-7.16 (t, J=8.0 Hz, 1H), 6.86-6.90 (m, 2H), 6.67-6.70 (m, 2H), 6.47-6.52 (td, J=2.4, 8.0 Hz, 2H), 6.39-6.41 (t, J=2.4 Hz, 1H), 4.75 (s, 1H), 3.62 (s, 2H).

Example 5 1,3-bis[3-(4-aminophenoxy)phenoxy]benzene (APB-1334) To a 300 mL round bottom flask equipped with stir bar, nitrogen inlet and condenser, 10.30 g (51.25 mmol) 3-(4-aminophenoxy)phenol, 8.25 g (25.00 mmol) 1,3-diiodobenzene, 95.2 mg (0.5 mmol) copper iodide, 123.1 mg (1.0 mmol) 2-picolinic acid, 31.84 g (0.15 mol) potassium phosphate were charged. After vacuum-back-filled with nitrogen for three times, 100 mL dimethylsulfoxide was charged. The mixture was heated to 90° C. in an oil bath and held for 16 hours. After cooled to room temperature, the mixture was poured into water. The mixture was extracted with 200 mL ethyl acetate for 3 times. The combined ethyl acetate layer was washed as 5% sodium carbonated solution, then, de-ionized water. After dried over anhydrous sodium sulfate, ethyl acetate was removed under reduce pressure to give crude product as brown oil. The crude product was further purified by silica gel chromatography, a mixture of methylene chloride/ethyl acetate 5:1 as eluent. 8.50 grams of product was obtained as light yellow solids after solvents was remove, 71.3% isolated yield, m.p. 100.2-102.8° C. $^1$H NMR (400Mz, CDCl$_3$): δ=7.17-7.25 (m, 3H), 6.85-6.89 (d, J=8.8 Hz, 4H), 6.60-6.73 (m, 13H), 3.54 (s, 4H). $^{13}$C NMR (101 MHz, CDCl$_3$) δ=160.33, 158.17, 157.80, 147.92, 142.96, 130.33, 130.18, 121.28, 116.18, 113.49, 112.37, 112.03, 109.49, 108.12. IR (cm-1): 3403, 3323, 3226, 3069, 3042, 3011, 1873, 1620, 1586, 1475, 1273, 1203, 1135, 1121, 983, 948, 843, 754, 693, 681, 503. Elemental analysis calculated for $C_{30}H_{24}N_2O_4$, C, 75.62; H, 5.08; N, 5.88; O, 13.43. Found: C, 75.56; H, 5.04; N, 5.86; O, 13.54.

Example 6 Synthesis of 1,4-bis[3-(4-aminophenoxy)phenoxy)]benzene (APPB-1434). To a 300 mL round bottom flask equipped with stir bar, nitrogen inlet and condenser, 5.15 g (25.60 mmol) 3-(4-aminophenoxy)phenol, 4.91 g (12.50 mmol) 1,4-diiodobenzene, 47.6 mg (0.25 mmol) copper iodide, 51.5 mg (0.50 mmol) 2-picolinic acid, 15.90 g (0.075 mol) potassium phosphate were charged. After vacuum-back-filled with nitrogen for three times, 25 mL dimethylsulfoxide was charged. The mixture was heated to 90° C. in an oil bath and held for 16 hours. After cooled to room temperature, the mixture was poured into water. The mixture was extracted with 200 mL ethyl acetate for 3 times. The combined ethyl acetate layer was washed as 5% sodium carbonated solution, then, de-ionized water. After dried over anhydrous sodium sulfate, ethyl acetate was removed under reduce pressure to give crude product as brown oil. The crude product was further purified by silica gel chromatography, a mixture of methylene chloride/ethyl acetate 5:1 as eluent. 5.2 grams of product was obtained as light yellow solids after solvents was remove, 87.3% isolated yield, m.p. 192.3-193.3° C. $^1$H NMR (400Mz, CDCl$_3$): δ=7.17-7.20 (t, J=4.0 Hz, 2H), 6.99 (s, 4H), 6.86-6.89 (d, J=8.8 Hz, 4H), 6.59-6.68 (m, 10H), 3.58 (s, 4H). $^{13}$C NMR (101 MHz, CDCl$_3$) δ160.33, 158.96, 152.39, 147.97, 142.97, 130.14, 121.31, 120.62, 116.19, 111.53, 111.40, 107.30. IR (cm-1): 3403, 3325, 3242, 3071, 3042, 1608, 1580, 1505, 1481, 1275, 1203, 1122, 971, 843, 761, 682, 494. Elemental analysis calculated for $C_{30}H_{24}N_2O_4$, C, 75.62; H, 5.08; N, 5.88; O, 13.43. Found: C, 75.73; H, 5.02; N, 5.89; O, 13.34.

Example 7 Synthesis of 1,3-bis[4-(4-aminophenoxy)phenoxy)]benzene (APPB-1344). To a 300 mL three neck round bottom flask equipped with stir bar, nitrogen inlet and condenser, 13.20 g (0.12 mmol) hydroquinone, 10.00 (0.25 mol) sodium hydroxide were charged. After vacuum-back-filled with nitrogen for three times, 50 mL dimethylsulfoxide and 50 mL de-ionized water were then charged. The mixture was heated to 50° C. in an oil bath and held at this temperature. 14.10 g (0.10 mol) 4-fluoro-1-nitrobenzene in 25 mL dimethylsulfoxide was added within 6 hours. After additional the mixture was held at 50° C. for 18 hours. After cooled to room temperature, the mixture was poured into 200 mL water. Solids were removed by filtration. The filtrate was neutralized by concentrate hydrochloric acid, until pH reach 6. The crude product was obtained by filtration. The crude product washed with de-ionized water, air convection dried. 20.9 grams product was obtained as light yellow crystals, 90.4% isolated yield, m.p. 171.8-173.7° C. $^1$H NMR (CDCl$_3$): δ=8.17-8.18 (d, J=8.8 Hz, 2H), 6.95-6.99 (dd, J=8.8 Hz, 4H), 6.88-6.90 (d, J=8.8 Hz, 2H), 5.12 (s, 1H).

Example 8 Synthesis of 4-(4-aminophenoxy)phenol. To a 300 mL round bottom flask equipped with stir bar, nitrogen inlet, 1.16 g (5.00 mmol) 4-(4-nitrophenoxy)phenol, 3.82 g (60.00 mmol) ammonium formate, 0.05 g 10% palladium on carbon was charged. After vacuum-back-filled with nitrogen for three times, 20 mL methanol was charged. The mixture was stirred at room temperature for 18 hours. After filtration, methanol was removed under reduced pressure. The crude product was washed de-ionized water, air convection dried. 0.84 grams of product was obtained as light pink crystals, 83.5% isolated yield, m.p. 153.1-154.3° C. $^1$H NMR (CDCl$_3$): δ=6.81-6.84 (m, 4H), 6.65-6.74 (m, 4H), 4.85 (s, 1H), 3.57 (s, 2H).

Example 9 Synthesis of 1,3-bis[4-(4-aminophenoxy)phenoxy)]benzene (APPB-1344). To a 300 mL round bottom flask equipped with stir bar, nitrogen inlet and condenser, 10.15 g (50.50 mmol) 4-(4-aminophenoxy)phenol, 8.25 g (25.00 mmol) 1,3-diiodobenzene, 47.6 mg (0.25 mmol) copper iodide, 64.4 mg (0.63 mmol) 2-picolinic acid, 21.23 g (0.10 mol) potassium phosphate were charged. After vacuum-back-filled with nitrogen for three times, 37.5 mL dimethylsulfoxide was charged. The mixture was heated to 90° C. in an oil bath and held for 16 hours. After cooled to room temperature, the mixture was poured into water. The mixture was extracted with ethyl acetate for three times. The ethyl acetate layer was washed with D-ionized water, and dried over anhydrous magnesium sulfate. After ethyl acetate was removed, the crude product was obtained as oil. The crude product was further purified by silica gel chromatography, ethyl acetate as eluent. The product was further purified by recrystallized by toluene/2-propanol. 5.30 grams of product was obtained as light pink crystals, 44.5% isolated yield, m.p. 123.9-125.1° C. $^1$H NMR (400Mz, CDCl$_3$): δ=7.17-7.21 (t, J=8.0 Hz, 1H), 6.85-6.97 (m, 12H), 6.60-6.67 (m, 7H), 3.56 (s, 4H). $^{13}$C NMR (101 MHz, CDCl$_3$) δ=159.52, 154.98, 150.95, 149.03, 142.65, 130.27, 120.85, 120.75, 118.61, 116.28, 111.78, 107.57. IR (cm-1): 3454, 3371, 3091, 3035, 3004, 1867, 1615, 1595, 1584, 1508, 1269, 1193, 1100, 970, 830, 768, 497. Elemental analysis calculated for $C_{30}H_{24}N_2O_4$, C, 75.62; H, 5.08; N, 5.88; O, 13.43. Found: C, 75.65; H, 5.07; N, 5.84; O, 13.34.

Example 10 Synthesis of 4-(3-iodophenoxy)-1-nitrobenzene. To 300 mL three necked round bottle flask, equipped with magnetic stir bar, nitrogen inlet, outlet 22.0 g (0.10 mol) 3-iodphenol, 14.8 g (0.11 mol) of 1-fluoro-4-nitrobenzene and 27.6 g (0.30 mol) potassium carbonated, were charged. After vacuum-back-filled with nitrogen for three times, 15 mL 1-methyl-2-pyrrolidinone was charged. The mixture as heated in an oil bath to 100° C. and held for 24 hours. After cooled to room temperature, the mixture was dilute with 300 mL ethyl acetate. Solids were removed via filtration. The filtrate was washed with di-ionized water three times. The ethyl acetate phase was dried over anhydrous sodium sulfate. After ethyl acetate was removed. The crude product was obtained as yellow oil, which recrystallized in ethanol to give light yellow crystals. 29.4 g finale product was obtained, 86.2% isolated yield, m.p. 84.0-85.0° C. $^1$H NMR (CDCl$_3$): δ=8.21-8.24 (dd, J=4.0, 9.2 Hz, 2H), 7.58-7.60 (d, J=8.0 Hz, 1H), 7.45 (s, 1H), 7.14-7.18 (t, J=8.0 Hz, 1H), 7.02-7.08 (m, 3H).

Example 11 Synthesis of 4-(3-iodophenoxy)-aniline. To a 300 mL round bottom flask equipped with stir bar, nitrogen inlet, 17.1 g (50.0 mmol) 4-(3-iodophenoxy)-1nitrobenzene, 56.4 g (0.25 mol) tin(II) chloride dihydrate were charged. After vacuum-back-filled with nitrogen for three times, 80 mL ethanol was charged. The mixture was heated in a 90° C. oil bath and held 3 hours. After cooled to room temperature, the mixture was poured into 40 sodium hydroxide in 400 mL water. The solids were filtrated washed with 300 mL ethyl acetate. The filtrate was extracted with 100 mL ethyl acetate for 3 times. The combined ethyl acetate layer was washed with de-ionized water and dried over anhydrous sodium sulfate. After ethyl acetate was removed, the crude product was obtained as yellow oil. The crude product was further purified by pass through as short silica gel chromatograph column, hexanes/ethyl acetate as eluent. The final product was obtained as yellow oil, solidified slowly into yellow solids in freezer. 12.0 grams of product was obtained, 77.1% isolated yield, m.p. 44.5-46.4° C. $^1$H NMR (CDCl$_3$): δ=7.32-7.34 (m, 1H), 7.23-7.24 (t, J=2.0 Hz, 1H), 6.90-7.00 (t, J=8.0 Hz, 1H), 6.83-6.90 (m, 3H), 6.65-6.69 (m, 2H), 3.60 (s, 2H).

Example 12 Synthesis of 4-(3-(4-(4-aminophenoxy)phenoxy)phenoxy)aniline (APPPA-4344). To a 100 mL round bottom flask equipped with stir bar, nitrogen inlet and condenser, 3.11 g (10.00 mmol) 4-(3-iodophenoxy)aniline, 2.21 g (11.00 mmol) 4-(4-aminophenoxy)phenol, 95.2 mg (0.50 mmol) copper iodide, 103.0 mg (1.00 mmol) 2-picolinic acid, 6.37 g (0.030 mol) potassium phosphate were charged. After vacuum-back-filled with nitrogen for three times, 10 mL dimethylsulfoxide was charged. The mixture was heated to 90° C. in an oil bath and held for 8 hours. After cooled to room temperature, the mixture was poured into water. Solids were harvested via filtration. The solids were washed with 5% sodium hydroxide solution, then de-ionized water. After air dried, the solids were obtained as crude product. The crude product was further purified by silica gel chromatography, methylene chloride, then methylene chloride/ethyl acetate 5:1 as eluent. The product was further purified by recrystallized from methanol, 1.70 grams of product was obtained as yellow crystals, 44.2% isolated yield, m.p. 126.5-128.5° C. $^1$H NMR (CDCl$_3$): δ=7.14-7.19 (m, 1H), 6.85-6.96 (m, 8H), 6.65-6.68 (m, 4H), 6.58-6.59 (m, 3H), 3.57 (s, 4H). $^{13}$C NMR (101 MHz, CDCl$_3$): δ=160.25, 159.33, 154.80, 151.07, 149.08, 148.06, 142.90, 142.53, 130.04, 121.26, 120.70, 120.66, 118.57, 116.22, 116.18, 111.20, 111.12, 107.08. IR (cm-1): 3431, 3406, 3354, 3331, 3228, 3064, 3042, 3012, 1622, 1608, 1587, 1495, 1275, 1209, 1200, 969, 844, 761, 683, 506, 482. Elemental analysis calculated for $C_{24}H_{20}N_2O_3$, C, 74.98; H, 5.24; N, 7.29; O, 12.49. Found: C, 74.95; H, 5.19; N, 7.24; O, 12.46.

Example 13 1,3-phenylenebis((4-(4-(4-aminophenoxy)phenoxy)phenyl)methanone) (APPKB-13444). To a 500 mL three necked round bottom flask equipped with Dean-Stark trap, condenser, stir bar and nitrogen inlet and outlet, 32.23 g (0.10 mmol) 1,3-phenylenebis((4-fluorophenyl)methanone), 42.22 g (0.21) 4-(4-aminophenoxy)phenol, 16.59 g (0.12 mmol) potassium carbonate were charged. After vacuum-back-filled with nitrogen for three times, 240 mL 1-methyl-2-pyrrolidinone was charged. The mixture was heated to 150° C., and held for 24 hours. After cooled to room temperature, the mixture was poured into 1000 mL 2-propanol, solids were harvested by filtration. The solids were washed with de-ionized water, then, 2-propanol, ethyl acetate and air convention dried. The solids were dissolved in hot toluene, and then, any insoluble solids were removed by filtration. After cooled to room temperature, crystals were formed and harvested by filtration. The crystals were washed with ethyl acetate. The final product was obtained as light yellow crystals, after the product was dried in vacuum oven at 120° C., 0.5 torr for 24 hours. 50.73 g product was obtained, 74.1% isolated yield, m.p. 168.3-179.3° C. $^1$H NMR (400 MHz, CDCl$_3$): δ=8.11 (t, J=1.6 Hz, 1H), 7.96-7.98 (dd, J=2.0, 8.0 Hz, 2H), 7.80-7.82 (d, J=8.8 Hz, 4H) 7.58-7.63 (t, J=7.6 Hz, 1H), 6.95-7.05 (m, 12H), 6.88-6.90 (d, J=8.4 Hz, 4H), 6.67-6.69 (d, J=8.8 Hz, 4H), 3.61 (s, 4H). $^{13}$C NMR (101 MHz, CDCl$_3$): δ=194.52, 162.63, 155.86, 149.50, 148.59, 142.83, 138.12, 132.90, 132.49, 130.90, 130.69, 128.41, 121.64, 120.93, 118.56, 116.50, 116.22. IR (cm-1): 3413, 3337, 3061, 3042, 3012, 1653, 1596, 1491, 1306, 1278, 1220, 1163, 1113, 999, 870, 846, 828, 817, 738, 699, 628, 502, 490. Elemental analysis calculated for $C_{44}H_{32}N_2O_6$, C, 77.18; H, 4.71; N, 4.09; O, 14.02. Found: C, 77.22; H, 4.66; N, 4.09; O, 14.00.

Examples 14-16 Synthesis and Characterization of polyimide oligomers from 4,4'-(ethyen-1,2-diyldiphthalic anhydride (EDPA) and various MPDA diamines. Four oligomers were made from EDPA as the dianhydride with 3 different diamines, endcaped either with phthalic anhydride (PA) or 4-phenylethynyl phthalic anhydride (PEPA). The degree of polymerization (X n) was kept as 12 by controlling feeding ratio of dianhydride vs diamine. The three diamines used in synthesis are 1,3-bis(3-(4-aminophenoxy)phenoxy)benzene (APPB-1334), 1,3-bis(4-(4-aminophenoxy)phenoxy)benzene (APPB-1344), and 4-(3-(4-(4-aminophenoxy)phenoxy)phenoxy)aniline (APPA-4344).

The structure of resulting PA- or PEPA-endcapped MPDA-EDPA oligoimides (n=12) are depicted below:

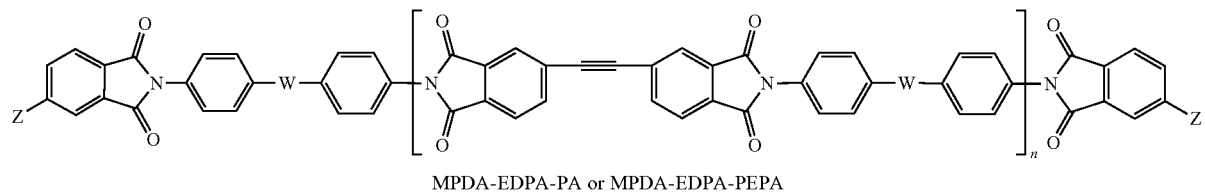

MPDA-EDPA-PA or MPDA-EDPA-PEPA

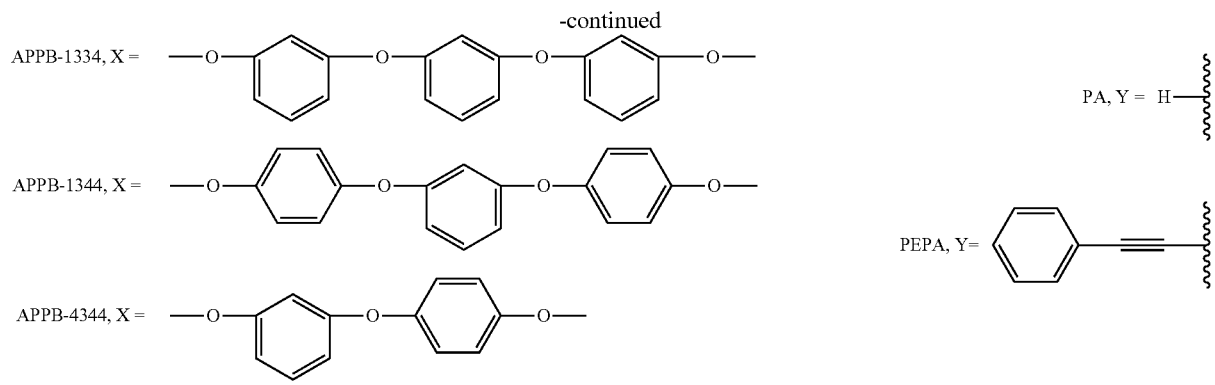

Example 14 EDPA-APPB(1344)-PEPA (07-46-2). To a 100 mL round-bottomed flask equipped with a magnetic stir bar and a nitrogen inlet, 1.0325 g (2.1667 mmol) of the diamine monomer, APPB-1334 and 10 mL of 1-methyl-2-pyrrolidinone (NMP) were charged. After APPB-1334 dissolved in NMP, 0.6365 g (2.0000 mmol) of the dianhydride monomer, EDPA was charged. The mixture was stirred for 8 hours, and 0.0827 (0.3333 mmol) of the endcapping agent, PEPA and additional 6 mL NMP were added to the polymerization mixture. Stirring of the mixture was continued at room temperature for 16 more hours. Then, 2.1 mL of acetic anhydride and 2.0 mL of pyridine were added to the reaction mixture, which was stirred at room temperature for another period of 16 hours. During this period, yellow solids gradually formed and precipitated. An additional 10 mL of NMP was added to facilitate stirring of the heterogeneous mixture. The mixture was heated to 80° C., kept at that temperature for 2 hours, and finally it was allowed to cool to room temperature. The mixture was poured into a beaker containing 400 mL of isopropanol (IPA), and crude solids were collected via filtration. The polymer product was washed sequentially with fresh IPA and acetone. After air drying in the filter funnel, the polymer was further dried in a vacuum oven at 130° C./0.5 torr for 24 hours.

Example 15 Synthesis of EDPA-APPB(1344)-PA (07-46-1). To a 100 mL round-bottomed flask equipped with a magnetic stir bar and a nitrogen inlet, 1.0325 g (2.1667 mmol) of the diamine monomer, APPB-1334 and 10 mL of 1-methyl-2-pyrrolidinone (NMP) were charged. After APPB-1334 had dissolved in NMP, 0.6365 g (2.0000 mmol) of the dianhydride monomer, EDPA was charged. The mixture was stirred for 8 hours, and 0.0494 g (0.3333 mmol) of the endcapping agent, phthalic anhydride (PA) and additional 6 mL NMP were added to the polymerization mixture. Stirring of the mixture was continued at room temperature for 16 more hours. Then, 2.1 mL of acetic anhydride and 2.0 mL of pyridine were added to the reaction mixture, which was stirred at room temperature for another period of 16 hours. During this period, yellow solids gradually formed and precipitated. An additional 10 mL of NMP was added to facilitate stirring of the heterogeneous mixture. The mixture was heated to 80° C., kept at that temperature for 2 hours, and finally it was allowed to cool to room temperature. The mixture was poured into a beaker containing 400 mL of isopropanol (IPA), and crude solids were collected via filtration. The polymer product was washed sequentially with fresh IPA and acetone. After air drying in the filter funnel, the polymer was further dried in a vacuum oven at 130° C./0.5 torr for 24 hours.

Example 16 Thermal and hot-stage polarized light microscopic characterization of PA- and PEPA endcapped MPDA-EDPA Oligo-imides. The oligomers were characterization by differential scanning calorimeter (DSC) and polarized optical microscope (POM). The results are summarized in Table 7. Based on DSC and POM results all oligomers exhibit crystalline phase. No liquid crystalline phase was found when cooling from isotropic phase. These results may indicate, EDPA monomer aspect ratio may not be high enough to stabilize liquid crystalline phase. Oligomer made from EDPA and APPB-1344 exhibit two crystalline phases. Further study is needed to confirm if the second crystalline phase is highly ordered liquid crystalline phase. Glass transition data also indicate, APPB-1334 is most flexible diamine and APPA-4344 is most rigid diamine.

TABLE 7

Summary of Thermal properties of PA- and PEPA endcapped MPDA-EDPA Oligoimides

| ID | MPDA Diamine | End Cap | $T_g$ (° C.) | $T_m$ (° C.) | $T_{L-i}$ (° C.) | $T_{i-L}$ (° C.) | $T_c$ (° C.) | $T_{Onset}$ (° C.) | $T_{peak}$ (° C.) | Phase |
|---|---|---|---|---|---|---|---|---|---|---|
| 07-46-1 | APPB-1334 | PA | 139.5 | 284.9 | ND | ND | 266.6 | 353.4 | 423.5 | Crystalline |
| 07-46-2 | APPB-1334 | PEPA | 140.0 | 288.5 | ND | ND | 270.2 | 350.9 | 418.9 | Crystalline |
| 07-48-1 | APPB-1344 | PEPA | 161.3 | 290.1 314.9 | ND | ND | 283.1 | 355.6 | 418.6 | 2× Crystalline (?) |
| 07-48-2 | APPA-4344 | PEPA | 193.3 | 311.9 363.5 | ND | ND | 318.2 | 370.2 | 409.7 | 2× Crystalline (?) |

Example 17-18. Synthesis and characterization of polyimide oligomers from a specific MPDA diamine, APPB-1334, and various mesogenic dianhydrides, L(DPA). Five oligomers were made from APPB-1334 as the MPDA diamine and four mesogenic dianhydrides, and endcapped with either PA or PEPA. The degree of polymerization (X n) was kept at 12 by controlling diamine/dianhydride/endcapper feeding ratio. The four mesogenic dianhydrides are

[1,1':4',1''-terphenyl]-3,3'',4,4''-tetracarboxylic dianhydride (TPDA), EDPA, 5-(4-((1,3-dioxo-1,3-dihydroisobenzofuran-5-yl)ethynyl)phenyl)isobenzofuran-1,3-dione (PEDPA), 5,5'-(1,4-phenylenebis(ethyne-2,1-diyl))bis(isobenzofuran-1,3-dione) (EPEDPA). The structures of these PA- or PEPA-endcapped L(DPA)-APPB(1334) oligoimides were shown below:

room temperature for additional 24 hours. The mixture was poured into a beaker of 2-propanol to precipitate the oligoimides. The product was collected on a filter funnel, washed with fresh 2-propanol, and air dried. Finally, the product was dried at 130° C. in a vacuum oven at 0.5 torr for 24 hours. The yield was quantitative.

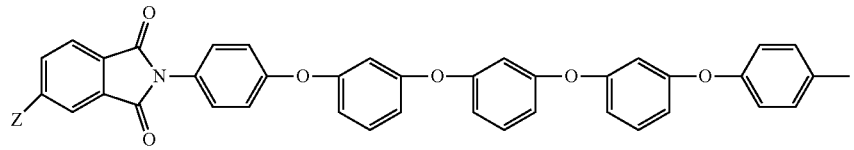

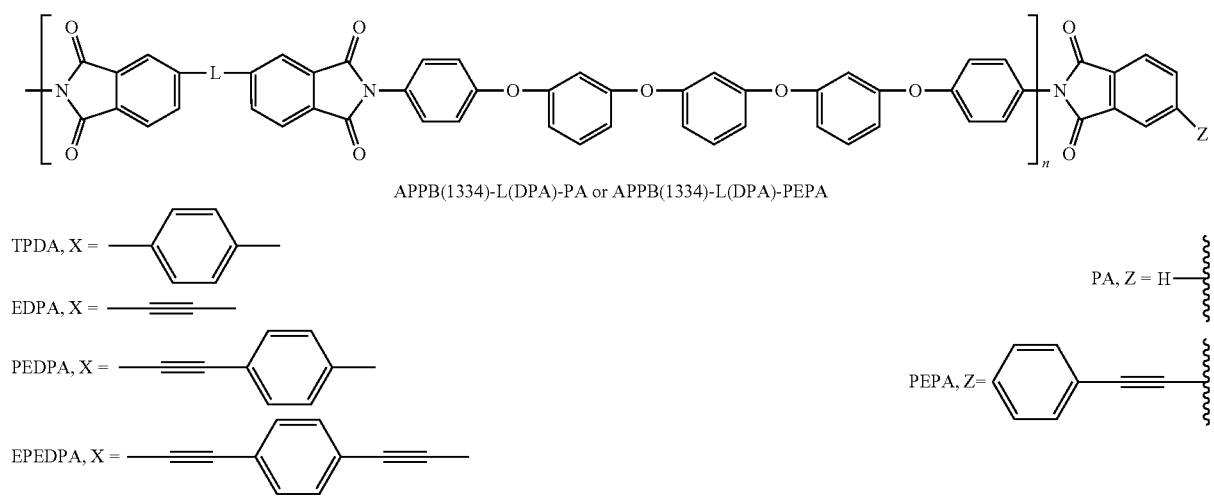

APPB(1334)-L(DPA)-PA or APPB(1334)-L(DPA)-PEPA

Example 17 Synthesis of EPDA-APPB(1334)-PA (07-46-1). To a 100 mL round-bottomed flask equipped with a stir-bar and a nitrogen inlet, 1.0325 g (2.167 mmol) of 1,3-bis[3-(4-aminophenoxy)phenoxy]benzene (APPB-1334) and 16 grams of 1-methyl-2-pyrollidinone were charged. The mixture was stirred at room temperature until all solids were dissolved. Then, 0.6365 g (2.000 mmol) of 4,4'-(ethyne-1,2-diyl)diphthalic anhydride (EDPA) was added. The mixture was stirred at room temperature for 8 hours before 49.4 mg (0.333 mmol) of phthalic anhydride (PA) was added. The mixture was further stirred for 16 hours at room temperature. Then, 2.0 mL of pyridine and 2.4 ml of acetic anhydride were added. The mixture was stirred at Example 18 Thermal and hot-stage polarized light microscopic characterization of APPB(1334)-L(DPA) oligoimides (n=12). The oligomers were characterization by differential scanning calorimeter (DSC) and polarized optical microscope (POM). The results were summarized in Table 8. Based on DSC and POM results all oligomers exhibit crystalline phase. Based on DSC curves and POM results, only oligomers with TPDA and PEDAP show the promising of forming liquid crystalline phase. Next step investigation will focus on confirmation if these two oligomers exhibit liquid crystalline phase by either x-ray diffraction pattern or rheology test results.

TABLE 8

Summary of thermal properties of PA-endcapped and PEPA-endcapped APPB(1334)-L(DPA) oligoimides (n = 12).

| ID | L(DPA) Dianhydride | End Cap | $T_g$ (° C.) | $T_m$ (° C.) | $T_{L\text{-}i}$ (° C.) | $T_{i\text{-}L}$ (° C.) | $T_c$ (° C.) | Phase |
|---|---|---|---|---|---|---|---|---|
| 07-17-2 | TPDA | PA | 154.1 | ND | 272.4 | 266.2 | ND | Crystalline & Liquid crystalline |
| 07-46-1 | EDPA | PA | 139.5 | 284.9 | ND | ND | 266.6 | Crystalline |
| 07-46-2 | EDPA | PEPA | 140.0 | 288.5 | ND | ND | 270.2 | Crystalline |
| 07-47-1 | PEDPA | PEPA | 143.7 | 252.6 | 266.0 | 250.3 | ND | Liquid Crystalline |

TABLE 8-continued

Summary of thermal properties of PA-endcapped and PEPA-endcapped APPB(1334)-L(DPA) oligoimides (n = 12).

| ID | L(DPA) Dianhydride | End Cap | $T_g$ (° C.) | $T_m$ (° C.) | $T_{L-i}$ (° C.) | $T_{i-L}$ (° C.) | $T_c$ (° C.) | Phase |
|---|---|---|---|---|---|---|---|---|
| 07-47-2 | EPEDPA | PEPA | 143.4 | 250.0 305.0 | ND | ND | 197.6 258.8 | 2× Crystalline |

Example 19 Synthesis of BPDA-APPA(4344)-PA (07-33-2) To a 100 mL round-bottomed flask equipped with a stir-bar and a nitrogen inlet, 0.6247 g (1.625 mmol) of 4-(3-(4-(4-aminophenoxy)phenoxy)phenoxy)aniline and 10 grams of 1-methyl-2-pyrollidine were charged. The mixture was stirred at room temperature until all solids were dissolved. 0.4413 g (1.500 mmol) 3,3',4,4'-Biphenyl tetracarboxylic dianhydride was charged. The mixture was stirred at room temperature for 8 hours before 37.3 mg (0.250 mmol) of phthalic anhydride was added. The mixture was further stirred for 16 hours at room temperature. Then, 2.0 mL pyridine and 2.4 ml acetic anhydride was added. The mixture was stirred at room temperature for additional 24 hours. The mixture was precipitated in 2-propanol. The solids was harvested via filtration and washed with fresh 2-propanol and air dried. The final product was further dried at 130° C. in a vacuum oven at 0.5 torr for 24 hours.

Example 20 Synthesis of TPDA-APPB(1344)-PA (07-22-1) To a 100 mL round-bottomed flask equipped with a stir-bar and a nitrogen inlet, 1.0325 g (2.167 mmol) of 1,3-bis[4-(4-aminophenoxy)phenoxy]benzene (APPB (1344) and 18 grams of 1-methyl-2-pyrrolidinone were charged. The mixture was stirred at room temperature until all solids were dissolved. 0.7406 g (2.000 mmol) of [1,1': 4',1"-terphenyl]-3,3",4,4"-tetracarboxylic dianhydride (TPDA) was added. The mixture was stirred at room temperature for 8 hours before 49.4 mg (0.333 mmol) of phthalic anhydride (PA) was added. The mixture was further stirred for 16 hours at room temperature. Then, 2.0 mL of pyridine and 2.4 mL of acetic anhydride were added. The mixture was stirred at room temperature for additional 24 hours. The mixture was poured into a beaker of 2-propanol to precipitate the oligo-imides. The product was collected on a filter funnel, washed with fresh 2-propanol and air dried. Finally, the oligomeric product was dried at 130° C. in a vacuum oven at 0.5 torr for 24 hours. The yield was quantitative.

Example 21 Synthesis of EDPA-APPB(1334)-PEPA (07-46-2) To a 100 mL round-bottomed flask equipped with a stir-bar and a nitrogen inlet, 1.0325 g (2.167 mmol) of 1,3-bis[3-(4-aminophenoxy)phenoxy]benzene, APPB-1334 and 16 grams of 1-methyl-2-pyrrolidinone were charged. The mixture was stirred at room temperature until all solids were dissolved. 0.6365 g (2.000 mmol) 4,4'-(ethyne-1,2-diyl)diphthalic anhydride (EDPA) was added. The mixture was stirred at room temperature for 8 hours before 82.7 mg (0.333 mmol) of 4-phenylethynylphthalic anhydride (PEPA) was added. The mixture was further stirred for 16 hours at room temperature. Then, 2.0 mL of pyridine and 2.4 mL of acetic anhydride was added. The mixture was stirred at room temperature for additional 24 hours. The mixture was poured into a beaker of 2-propanol to precipitate the oligo-imides. The product was collected on a filter funnel, washed with fresh 2-propanol, and air dried. Finally. the oligo-imide product was dried at 130° C. in a vacuum oven at 0.5 torr for 24 hours. The product yield was quantitative.

Example 22 Synthesis of PEDPA-APPB(1334)-PEPA (07-47-1, 08-71-1) To a 100 mL round-bottomed flask equipped with a stir-bar and a nitrogen inlet, 1.0325 g (2.167 mmol) of 1,3-bis[3-(4-aminophenoxy)phenoxy)]benzene, APPB-1334, and 16 grams of 1-methyl-2-pyrolidinone were charged. The mixture was stirred at room temperature until all solids were dissolved. 0.7887 g (2.000 mmol) of 4'-((3, 4-dicarboxyphenyl)ethynyl)phenyl-3,4-dicarboxylic dianhydride (PEDPA) charged. The mixture was stirred at room temperature for 8 hours before 82.7 mg (0.333 mmol) of 4-phenylethynylphthalic anhydride (PEPA) was added. The mixture was further stirred for 16 hours at room temperature. Then, 2.0 mL pyridine and 2.4 ml acetic anhydride was added. The mixture was stirred at room temperature for additional 24 hours. The mixture was precipitated in 2-propanol. The solids was harvested via filtration and washed with fresh 2-propanol and air dried. The final product was further dried at 130° C. in a vacuum oven at 0.5 torr for 24 hours.

Example 23 Synthesis of EPEDPA-APPB(1334)-PEPA (07-47-2) To a 100 mL round-bottomed flask equipped with a stir-bar and a nitrogen inlet, 1.0325 g (2.167 mmol) of 1,3-bis[3-(4-aminophenoxy)phenoxy)]benzene, APPB-1334 and 18 grams of 1-methyl-2-pyrrolidinone were charged. The mixture was stirred at room temperature until all solids were dissolved. 0.8367 g (2.000 mmol) of 4,4'-(1,4-phenylenebis(ethyne-2,1-diyl))diphtalic anhydride (EPEDPA) was charged. The mixture was stirred at room temperature for 8 hours before 82.7 mg (0.333 mmol) of 4-phenylethynylphthalic anhydride was added. The mixture was further stirred for 16 hours at room temperature. Then, 2.0 mL of pyridine and 2.4 mL of acetic anhydride were added. The mixture was stirred at room temperature for additional 24 hours. Then, the resulting reaction mixture was poured into a beaker of 2-propanol to precipitate the oligo-imides. The product was collected on a filter funnel, washed with fresh 2-propanol, and air dried. Finally, the oligo-imide product was dried at 130° C. in a vacuum oven at 0.5 torr for 24 hours. The product yield was quantitative.

Example 24 Synthesis of TPDA-APKB(1344)-PA (07-56-1) To a 100 mL round-bottomed flask equipped with a stir-bar and a nitrogen inlet, 1.0845 g (2.167 mmol) of 1,3-bis[4-(4-aminophenoxy)benzoyl]benzene, APKB-1344, and 18 grams of 1-methyl-2-pyrrolidionne were charged. The mixture was stirred at room temperature until all solids were dissolved. 0.7406 g (2.000 mmol) of [1,1':4',1"-terphenyl]-3,3",4,4"-tetracarboxylic dianhydride (TPDA) was charged. The mixture was stirred at room temperature for 8 hours before 49.4 mg (0.333 mmol) of phthalic anhydride (PA) was added. The mixture was further stirred for 16 hours at room temperature. Then, 2.0 mL of pyridine and 2.4 mL of acetic anhydride were added. The mixture was stirred at room temperature for additional 24 hours. At the end of reaction, any large particles in the mixture were grounded into fine paste with a spatula before the mixture was poured into a beaker of 2-propanol to precipitate the oligo-imides.

The product was collected on a filter funnel, washed with fresh 2-propanol, and air dried. Finally, the oligo-imide product was dried at 130° C. in a vacuum oven at 0.5 torr for 24 hours. The product yield was quantitative.

Example 25 Synthesis of PEDPA-APKB(1344)-PEPA (08-71-2) To a 100 mL round-bottomed flask equipped with a stir-bar and a nitrogen inlet, 1.0845 g (2.167 mmol) of 1,3-bis[4-(4-aminophenoxy)benzoyl]benzene, APKB-1344 diamine, and 18 grams of 1-methyl-2-pyrrolidinone were charged. The mixture was stirred at room temperature until all solids were dissolved. 0.7887 g (2.000 mmol) of 4'-((3, 4-dicarboxyphenyl)ethynyl)phenyl-3,4-dicarboxylic dianhydride (PEDPA) was then added. The mixture was stirred at room temperature for 8 hours before 82.7 mg (0.333 mmol) of 4-phenylethynylphthalic anhydride (PEPA) was added. The mixture was further stirred for 16 hours at room temperature. Then, 2.0 mL of pyridine and 2.4 ml of acetic anhydride were added. The mixture was stirred at room temperature for additional 24 hours. At the end of reaction, any large particles in the mixture were grounded into fine paste with a spatula before the mixture was poured into a beaker of 2-propanol to precipitate the oligo-imides. The product was collected on a filter funnel, washed with fresh 2-propanol, and air dried. Finally, the oligo-imide product was dried at 130° C. in a vacuum oven at 0.5 torr for 24 hours. The product yield was quantitative.

Example 26 Synthesis of BTDA-APPKB(13444)-PA (07-68-2) To a 100 mL round-bottomed flask equipped with a stir-bar and a nitrogen inlet, 1.4836 g (2.167 mmol) of 1,3-phenylenebis((4-(4-(4-aminophenoxy)phenoxy)phenyl) methanone), APPKB-13444 diamine, and 20 grams of 1-methyl-2-pyrrolidinone were charged. The mixture was stirred at room temperature until all solids were dissolved. Then, 0.6444 g (2.000 mmol) of 3,3', 4,4'-benzophenone tetracarboxylic dianhydride (BTDA) was added. The mixture was stirred at room temperature for 8 hours before 49.4 mg (0.333 mmol) of phthalic anhydride (PA) was added. The mixture was further stirred for 16 hours at room temperature. Then, 2.0 mL of pyridine and 2.4 ml of acetic anhydride were added. The mixture was stirred at room temperature for additional 24 hours. At the end of reaction, any large particles in the mixture were grounded into fine paste with a spatula before the mixture was poured into a beaker of 2-propanol to precipitate the oligo-imides. The product was collected on a filter funnel, washed with fresh 2-propanol, and air dried. Finally, the oligo-imide product was dried at 130° C. in a vacuum oven at 0.5 torr for 24 hours. The product yield was quantitative.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and process, and illustrative examples shown and described. Accordingly, departures may be made from such details without departing from the scope of the general inventive concept.

What is claimed is:

1. A molecule having the following formulae:

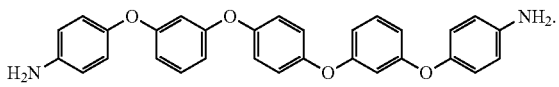 [SMILES: Nc1ccc(Oc2cccc(Oc3ccc(Oc4cccc(Oc5ccc(N)cc5)c4)cc3)c2)cc1]

* * * * *